(12) United States Patent
Janevski et al.

(10) Patent No.: US 9,858,392 B2
(45) Date of Patent: Jan. 2, 2018

(54) MEDICAL ANALYSIS SYSTEM

(75) Inventors: Angel J. Janevski, New York, NY (US); Nevenka Dimitrova, Pelham Manor, NY (US); Sitharthan Kamalakaran, Huntington, NY (US); Yasser Alsafadi, Yorktown Heights, NY (US); Nilanjana Banerjee, Armonk, NY (US); Anca Ioana Daniela Bacur, Eindhoven (NL); Jasper Van Leeuwen, Eindhoven (NL); Vinay Varadan, Hastings on Hudson, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1875 days.

(21) Appl. No.: 12/992,169

(22) PCT Filed: May 6, 2009

(86) PCT No.: PCT/IB2009/051862
§ 371 (c)(1),
(2), (4) Date: Nov. 11, 2010

(87) PCT Pub. No.: WO2009/138909
PCT Pub. Date: Nov. 19, 2009

(65) Prior Publication Data
US 2011/0077964 A1    Mar. 31, 2011

Related U.S. Application Data

(60) Provisional application No. 61/052,462, filed on May 12, 2008.

(51) Int. Cl.
*G06Q 10/00* (2012.01)
*G06F 19/00* (2011.01)
*G06Q 50/22* (2012.01)

(52) U.S. Cl.
CPC ......... *G06F 19/3443* (2013.01); *G06Q 50/22* (2013.01)

(58) Field of Classification Search
CPC ................. G06F 19/3443; G06Q 50/22–50/24
(Continued)

(56) References Cited

U.S. PATENT DOCUMENTS

| 8,135,595 B2 * | 3/2012 | Dalton ............................. 705/2 |
| 2002/0010552 A1 * | 1/2002 | Rienhoff et al. ................ 702/19 |

(Continued)

FOREIGN PATENT DOCUMENTS

WO    20070137187 A2    11/2007

OTHER PUBLICATIONS

Hoon, S., et al.; Biopipe: a flexible framework for protocol-based bioinformatics analysis; 2003; Genome Research; 13(8)1904-1915.
(Continued)

*Primary Examiner* — Sheetal R Paulson

(57) ABSTRACT

The present invention relates to effective diagnosis of patients and assisting clinicians in treatment planning. In particular, invention provides a medical analysis system that enables refinement of molecular classification. The system provides a molecular profiling solution that will allow improved diagnosis, prognosis, response prediction to provide the right chemotherapy, and follow-up to monitor for cancer recurrence.

20 Claims, 32 Drawing Sheets

(58) Field of Classification Search
USPC .................................................. 705/2–3
See application file for complete search history.

(56) References Cited

U.S. PATENT DOCUMENTS

2006/0173663 A1    8/2006   Langheier et al.
2009/0299645 A1*  12/2009   Colby et al. ............... 702/19

OTHER PUBLICATIONS

Gentleman, R. C., et al.; Bioconductor: open software development for computational biology and bioinformatics; 2004; Genome Biology; 5(10)R80.

Diaz-Uriarte, et al.; Asterias: integrated analysis of expression and aCHG data using an open-source, web-based, parallelized software suite; 2007; vol. 35; W75-W80.

Vaquerizas, J. M., et al.; GEPAS, an experiment-oriented pipeline for the analysis of microarray gene expression data; 2005; vol. 33; W616-W620.

Dugas, M., et al.; A comprehensive leukemia database: integration of cytogenetics, molecular genetics and microarray data with clinical information, cytomorphology and immunophenotyping; 2001; Leukemia; Macmillan Press Ltd.; pp. 1805-1810.

Saltz, J., et al.; caGrid: design and implementation of the core architecture of the cancer biomedical informatics grid; 2006; Bioinformatics; 22(15)1910-1916.

Lingjaedre, O. C., et al.; CGH-Explorer: a program for analysis of array-CGH data; 2005; Bioinformatics; 21(6) 821-822.

West, M., et al.; Embracing the complexity of genomic data for personalized medicine; 2006; Genome Research; 16(5)559-566.

Spang, R.; Diagnostic signatures from microarrays: a bioinformatics concept for personalized medicine; 2003; Biosilico; Elsevier; pp. 64-68.

Hariharaputran, S., et al.; VINEdb: a data warehouse for integration and interactive exploration of life science data; 2007; J. of Integrative Bioinformatics; 4(3):63.

Van 'T Veer, L. J., et al.; Gene expression profiling predicts clinical outcome of breast cancer; 2002; Nature; vol. 415; 530-536.

Olivotto, I. A., et al.; Population-Based Validation of the Prognostic Model ADJUVANT! for Early Breast Cancer; 2005; Journal of Clinical Oncology; 23(12)2716-2725.

Paik, S., et al.; Gene Expression and Benefit of Chemotherapy in Women with Node-Negative, Estrogen Receptor-Positive Breast Cancer; 2006; Journal of Clinical Oncology; 24(23)1-12.

Ravdin, P.; Assessing Adjuvant Benefit: Adjuvant Decision Making in the Era of Evidence-Based Medicine and a Broad Array of Options; 2005; Summary Proceedings: 29th Annual Symposium of the American Society of Breast Disease; 1-4.

\* cited by examiner

MEDICAL ANALYSIS SYSTEM

CROSS REFERENCE TO RELATED APPLICATIONS

This application claims the benefit of U.S. provisional application Ser. No. 61/052,462 filed May 12, 2008, which is incorporated herein by reference.

TECHNICAL FIELD OF THE INVENTION

The present invention relates to a medical analysis system. In particular the present invention relates to a corresponding process and a corresponding computer program product.

BACKGROUND OF THE INVENTION

Breast cancer is a complex genetic disease driven by the accumulation of multiple molecular alterations. Recent molecular advances in high-throughput genomic, transcriptomic and epigenomic technologies have made it possible to focus on the molecular complexity of breast cancer and help guide cancer prognostication and therapy prediction.

Perou et al. demonstrated that breast cancer can be classified into distinct groups based on their gene expression profiles. The Estrogen Receptor positive (ER+) group is characterized by higher expression of a panel of genes that are typically expressed by breast luminal epithelial cells ('luminal' cancer). The ER− branch covered three subgroups of tumors: 1) overexpressing ERBB2 (HER2); 2) expressing genes characteristic of breast basal cells (basal-like cancer); and 3) normal-like samples. The clinical importance is that ER+ tumors typically show good prognosis and basal-like and HER2 tumors have poor prognosis.

Gene expression profiling has also led to the development of two gene-expression assays, Oncotype DX and MammaPrint, which determine the risk of breast cancer recurrence in patients for early stage node-negative breast cancer. Oncotype DX analyzes the expression of 21 genes and calculates a recurrence score to identify the likelihood of cancer recurrence in patients and an assessment of their likely benefit from chemotherapy. MammaPrint analyzes the expression of 70 genes and allows patients (<61 years) with early-stage breast cancer to be categorized as having a high or low risk of distant metastasis. High-risk patients may then be managed with more aggressive therapy.

Many other molecular profiling technologies are used to address similar clinical questions. Representational Oligonucleotide Microarray Analysis (ROMA) detects genomic amplifications and deletions and has enabled detection of certain copy number variation patterns and measures their correlation to patient survival.

Following a cancer diagnosis such as breast cancer and primary treatment of localized cancer, a doctor has many options for therapy. How can the 'right' decision for treatment be made? Traditionally, diagnostic imaging has played a critical role in cancer treatment choice by characterizing the location, morphology and spread of the tumor. Cancer is correlated with changes within the DNA and its regulatory potential, and the specific characteristics of the patient's tumor cell molecular profile can direct a clinician to the 'right' therapy.

Today, molecular tests categorize patients based on single-gene tests like the aforementioned ER, PR and HER2 gene expression. However, there is still significant variation in treatment response within tumors with similar clinical classification and scope for improved tests using DNA methylation and gene expression. DNA methylation affects gene regulation without change in the genetic code. Abnormal DNA methylation profiles are associated with diseases like cancer. Gene expression profiling assess gene activity at the level of a whole genome.

Several small startups and big companies operate in the area of molecular therapy planning, such as Agendia (MammaPrint™ is a prognostic test) and Genomic Health (Oncotype Dx). The target area of these companies is patient stratification for chemotherapy for subsets of breast cancer patients (such as patients who have lymph node negative, ER positive tumors). In addition there is Adjuvant!, which focuses on providing decision support and therapy planning services using clinical factors such as age, tumor size, node status, grade.

Further refinement in molecular classification however, can result in differing clinical significance. Hence, there is a clinical need for molecular profiling solutions that will provide improved diagnosis, prognosis, response prediction to provide the right chemotherapy, and follow-up to monitor for cancer recurrence.

Hence, an improved medical decision tool or system would be advantageous, and in particular a more efficient and/or reliable system would be advantageous.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide a medical analysis system that solves the above mentioned problems of the prior art with finding the appropriate treatment for one or more patients in a fast and/or reliable manner.

Thus, an object of the present invention relates to effective diagnosis of patients and assisting clinicians in treatment planning. In particular, it is an object of the present invention to provide a medical analysis system that solves the above mentioned problems of the prior art in obtaining this and other objects.

Thus, the first aspect of the invention relates to a medical analysis system for pre-clinical and/or clinical analysis of data obtained from at least one patient, the system comprising:

an internal database (IDB), the database comprising a collection of data, analysis results, flow definitions, and tool definitions, and other related data for tools that utilize a database repository, a database access unit (DA), the unit being adapted for providing access to the internal database, a flow definition unit (FD), the unit providing execution of a configurable flow of analysis and visualization of a plurality of data modalities, the plurality of data modalities comprising:

a first bio-molecular modality comprising bio-molecular data related to the patient, and a second clinical modality comprising clinical data related to the patient, a tool execution engine (TEE), having an interface for the system to configure and instantiate one or more tools working on one or more of the data modalities, a tool repository, the repository comprising a collection of tools for which the system is configured to execute, said tools complying with a set of rules in order for it to be possible to visualize their execution in a graphical user interface (GUI), one or more associated external databases (EDB), the external database(s) representing data stored in the said system itself, or in a database different from the said internal database (IDB), and a graphical user interface (GUI), said interface simultaneously visualizing data, analysis results, and outcome of one or more tool executions, and wherein said interface is further adapted for simultaneously visualizing:
1) an outcome of said first bio-molecular modality, and
2) an outcome of said second clinical modality.

The invention is particularly, but not exclusively, advantageous for obtaining a multimodal approach for designing personalized therapy. The invention thereby facilitate a fully integrated genomic design and analysis toolbox, which enables access to clinical information about the patient along with pertinent molecular information (e.g. gene expression as well as differential DNA methylation).

Furthermore, the invention facilitate integration of multiple machine learning tools specialized in a) gene expression profiling, b) DNA methylation profiling, c) combining clinical parameters with molecular level information, d) combining with clinical, biological knowledge with molecular data, and/or d) integration of molecular modalities by statistical tools.

The invention allows for a configurable flow of execution of bioinformatic tools facilitating advanced means to analyze data of multiple modalities and to browse the data and the results from the signature-discovery processes. It provides a lightweight interface to a (dynamic set of) new and existing tools and allows them to be executed with little or no modification.

The advantage of this solution is rapid implementation and execution of analysis processes and ease of communicating methods and results clinicians and other interested parties.

The system according to the first aspect may be applied to at least one patient in an in pre-clinical situation. One advantage is that the data and the information on the patient may be used be the system to discover bio-molecular signatures. Another advantage of doing so is that the system may integrate the data of the patient in system in order to expand the data available.

The system according to the first aspect may also be applied to a group of patients.

The system according to the first aspect may be applied to one patient in a clinical situation. Thereby the system enables the physician to identify any bio-molecular/clinical signatures in the data of the patient thereby assisting the diagnosis and further treatment of the patient.

In line with the previous, the system according to the first aspect may be function may also function as a clinical decision support system (CDS).

The system according to the first aspect also may be configured such that said first bio-molecular modality and said second clinical modality is integrateable by a machine learning algorithm, the result of said integration being visualizable in the graphical user interface. The major advantage of this set up is that it enables the discovery of complex bio-molecular signatures in very large and complex data collections.

Further, the system according to the first aspect also may be configured such that said first bio-molecular modality and said second clinical modality is integrateable by a statistical algorithm, the result of said integration being visualizable in the graphical user interface.

The system according to the first aspect also may be configured such said that first bio-molecular modality and said second clinical modality is integrateable based on their respective genomic annotation, the result of said integration being visualizable in the graphical user interface.

In a further embodiment, the system according to the first aspect may be configured such that said first bio-molecular modality is based on a high-throughput data sampling modality. The system thereby enables the analysis of high-throughput data in a context including data of other modalities.

The system according to the first aspect may be configured such that the sample provided by said high-throughput data sampling modality comprise data on at least 100.000 parameter/species.

The system according to the first aspect may also be configured such that said first bio-molecular modality is selected from the group consisting of a high-throughput gene expression profiling, DNA methylation status profiling, comparative genomic hybridization analysis. These modalities generate large and complex data sets which may be applied to the system and used to identify bio-molecular signatures across the modalities.

In one particular version of the system according to the first aspect, said flow definition unit (FD) comprises at least one further bio-molecular modality. The version of the system integrates more bio-molecular modalities.

In a further version of the system according to the first aspect, said further bio-molecular modality is selected from the group consisting of a high-throughput gene expression profiling, DNA methylation status profiling, comparative genomic hybridization analysis, and SNP profile.

In the system according to the first aspect the patient may have a clinical condition selected from the group consisting cancer, a cardiovascular disease, a metabolic disease, a gastro-intestinal disease, a neurological disease. One advantage of this system is that is enables the use of the system to discover bio molecular and clinical signature associated with a specific clinical condition and subsequently application of the system and signature in a clinical setting.

In a second aspect, the present invention relates to a process for the discovery of bio-molecular or clinical signature associated with a specific clinical condition comprising the use of the medical analysis system according to the first aspect of the invention.

The invention is particularly, but not exclusively, advantageous for discovering of bio-molecular or clinical signature related to clinical condition is selected from the group consisting of cancer, a cardiovascular disease, a metabolic disease, a gastro-intestinal disease, a neurological disease.

More particular, not exclusively, advantageous the process may be discovering of bio-molecular or clinical signature related breast cancer or colon cancer. Breast cancer and colon cancer are known to correlate with aberrant gene expression profiles/DNA methylation profiles.

Further, the process according to the second aspect may be for the discovery of a signature selected from the group consisting of gene expression signature, DNA methylation status signature, comparative genomic hybridization signature and SNP signature. These modalities typically generates large amount of data which requires high capacity system to reveal any bio-molecular present.

In a third aspect, the present invention relates to a process for clinical decision support comprising the use of the medical analysis system according to the first aspect of the invention.

The invention also provides that the data of a patient is applied to the system for identification of a bio-molecular or clinical signature associated with a clinical condition. The advantage of this embodiment is that the application of the bio-molecular/clinical signature may be used to indicate whether a patient is likely suffer from a clinical condition associated with said signature.

In a fourth aspect, the invention relates to a computer program product being adapted to enable a computer system comprising at least one computer having data storage means associated therewith to control an analysis process according to the second aspect of the invention.

This aspect of the invention is particularly, but not exclusively, advantageous in that the present invention may be implemented by a computer program product enabling a computer system to perform the operations of the second aspect of the invention. Thus, it is contemplated that some known medical analysis system may be changed to operate according to the present invention by installing a computer program product on a computer system controlling the said medical analysis system. Such a computer program product may be provided on any kind of computer readable medium, e.g. magnetically or optically based medium, or through a computer based network, e.g. the Internet.

The first, second, third and fourth aspect of the present invention may each be combined with any of the other aspects. These and other aspects of the invention will be apparent from and elucidated with reference to the embodiments described hereinafter.

BRIEF DESCRIPTION OF THE FIGURES

The present invention will now be explained, by way of example only, with reference to the accompanying Figures, where

FIGS. 23 and 24 shows an example of a screen related to a multimodal correlation feature analysis—text output.

Figure 1A:
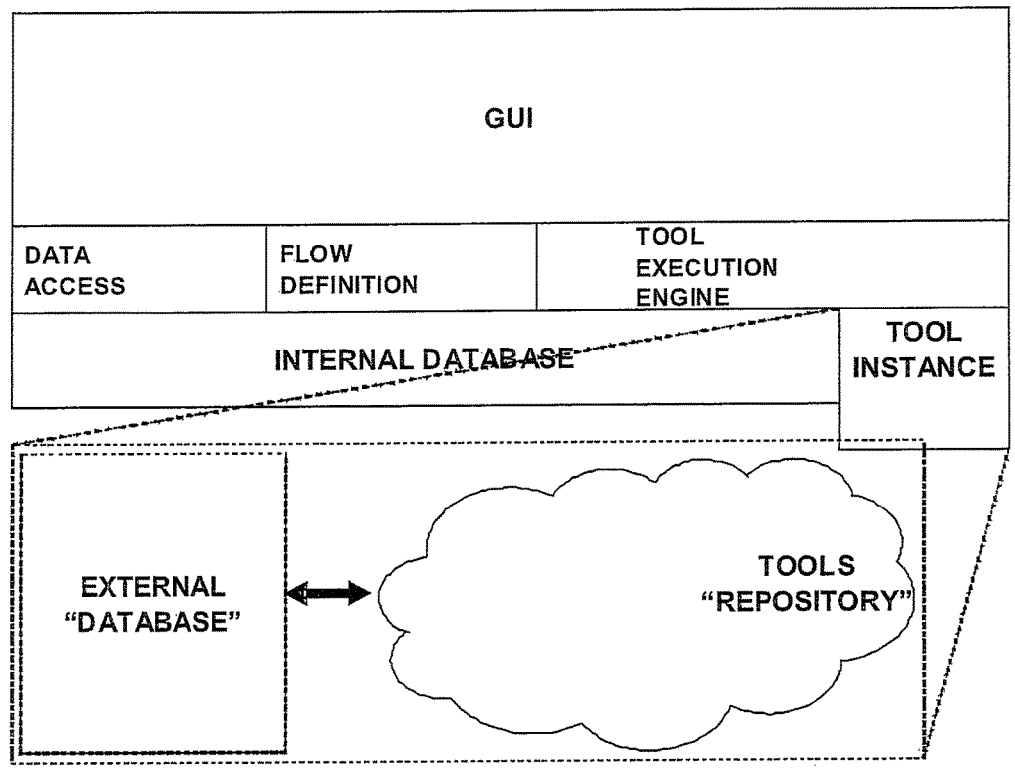
FIG. 1 shows the architecture of the system.

The present invention will now be described in more detail in the following.

DETAILED DESCRIPTION OF THE INVENTION

There is a need for translational clinical tools based on molecular bioinformatics, particularly in current cancer care. The inventors disclose with the present invention a tool for clinical decision making that relies on genomic and epigenomic measurement modalities as well as clinical parameters such as histopathological results and survival information.

An object of the present invention is to facilitate discovery of molecular profiles of clinical conditions and enable their use in a clinical setting. The present invention describes new technologies to obtain genomic information from tissue specimen and to assist diagnosis, determination of the appropriate therapy, and follow-up.

The inventor's Physician Accessible Preclinical Analytics Application (PAPAyA) integrates a powerful set of statistical and machine learning tools that could leverage the connections among the different modalities. The system is easily extendable and reconfigurable to support integration of existing research methods and tools into powerful data analysis pipelines. PAPAyA enables analysis of data from clinical studies, formulation of new clinical hypotheses, and facilitates clinical decision support by abstracting molecular profiles for clinicians. A current configuration of PAPAyA with examples of its performance on breast cancer molecular profiles is used to present the system in action.

The inventors present a multimodal molecular approach for designing personalized therapy. In particular, the method focuses on tumor subtyping and identifies patient subpopulations that would most likely respond to chemotherapy (e.g. Herceptin) leading to a predictive diagnostic test.

The inventors provide a prototype of genomic design and analysis toolbox that improves preclinical discovery of molecular profiles that characterize samples of breast and ovarian cancer patient biopsies. The inventors also provide results from a set of decision analysis tools that aid in patient stratification and predict therapy response.

The system of the invention provides a configurable platform that enables analysis and interpretation of results around clinical studies based on high-throughput molecular measurements. The system of the invention combines bioinformatics software methods to be used for translational research, pre-clinical, and parts for clinical applications. The system of the invention covers the following aspects:

Integrating analysis of multiple modalities to infer correlated information about most important genes/loci that may contribute to outcome and patient status (and will be used for therapy response). The inventors provide the incorporation of patient information from gene expression and DNA methylation in addition to clinical parameters such as histological grade, node, ER/PR status, and outcome.

Combining various machine learning tools to analyze this data (beyond description of such tools in the literature)

Use of such integrated analysis for diagnosis, prognosis, therapy response, and follow-up.

The inventors provides results from a set of decision analysis tools to browse through patient information and gene signatures and individually analyze gene expression profiles as well as differential DNA methylation profiles as well as to make inferences based on correlation and co-ocurrence. These tools rely both on high-throughput gene expression profiling as well as other clinical predictive and prognostic indices based on patient information such as tumor size, hormonal and histopathological parameters.

The inventors provide these tools and results using the Genomic Design and Analysis Toolbox (GDAT), called Papaya, that contains methods that help in the preclinical discovery phase for breast and ovarian cancer. Specifically, these tools include feature subset selection, classification, clustering methods and top-down hierarchical sorting as well as decision analysis, incorporating biological knowledge about protein-DNA interactions, clinical prognostic indices, DNA methylation and gene expression profiling data. We present results from GDAT leveraging multiple molecular modalities, for example high-throughput gene expression profiling and DNA methylation profiling, to further improve diagnostics.

The systems of the invention provide a comprehensive view by combining discovered molecular signatures with imaging and additional clinical information. Further, the system may be employed as an assisting tool in forming diagnosis, selecting treatment direction (e.g. hormone or chemotherapy) and the appropriate monitoring the progress and follow-up of the disease. The system may also be used to provide molecular information packages (e.g. combined molecular signatures with corresponding meta data) as a service to clinicians or to third-party decision support systems. Moreover, the system may be used to develop and provide molecular-medicine-enhanced clinical guidelines that can be customized to a patient's molecular profile.

Some of the challenges with high-throughput genomic data analysis lie in coping with high measurement and biological noise, a huge number of features and limited patient samples. The present invention provides statistically-rigorous approach of utilizing multiple molecular modalities and clinical information, which is likely to eliminate many spurious signals, so that we can focus on the underlying biology of the disease.

Fusion of more traditional clinical predictors of outcome with molecular information (e.g. methylation and gene expression) from the tumors themselves is considered useful, but learning how to interpret probabilistic information and communicate results with physicians and patients is a major challenge. The solution to the problem is provided with the present invention. The system may assist the application of personalized medicine in the clinic.

There is a clear clinical need for an integrated decision support system that takes into account clinical, histopathological, and molecular profiles of the patient. Such a system will provide a one-stop solution to aid informed decision making by the tumor board (radiologist, pathologist, surgeon, radiotherapist and oncologist).

The description above is primarily of an embodiment for pre-clinical use for clinical research. In another embodiment, this invention can be similarly used as a clinical application.

The System

The architecture of the present system has the following components, cf. also FIG. 1A;

GUI: the Graphical User Interface combines components that show synchronously data, analysis results, and outcome of tool executions.

DATA ACCESS (DA): Provides access to the database of study information, measurements, and analysis results.

FLOW DEFINITION (FD): Provides execution of the configurable flow of genomic data analysis and clinical/molecular data-browsing steps.

TOOL EXECUTION ENGINE (TEE): Provides interface for the application to seamlessly configure and instantiate tools from various platforms. This allows application extension with new tools to be easily added to the configuration and the flow with little or no modification.

INTERNAL DATABASE IDB): Collection of study data, analysis results, the flow and tool definitions, and any other data for the external tools that utilize a database repository.

TOOL "REPOSITORY" (TR): The collection of tools for which the application is configured to execute. These tools comply with the basic set of rules in order for it to be possible to visualize their execution.

EXTERNAL "DATABASE" (EDB): The collection of all data and other files that the external tools use stored somewhere on the file system or in a database different from the IDB.

Figure 1B:
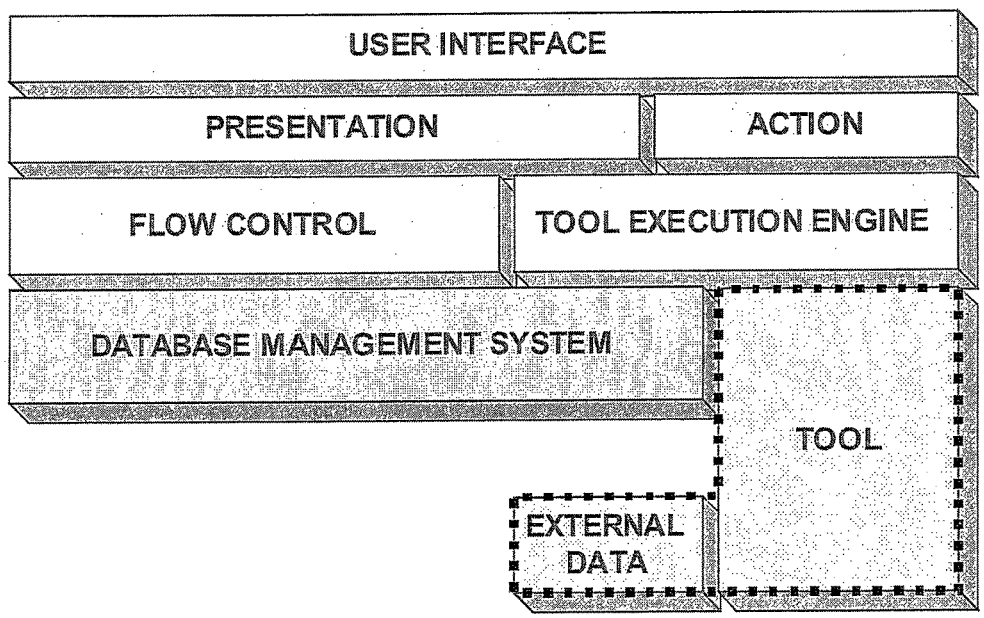

A slightly modified architecture of the present system is illustrated in FIG. 1B, where flow definition (FD) and data access (DA) of FIG. 1A is combined into flow control of FIG. 1B. Similarly, the general user interface (GUI) is subdivided into modules of user interface, presentation and action as shown in FIG. 1B. The lower structure is also slightly modified as shown in FIG. 1B, where a database management system is shown together with the modules "tools" and "external data".

Accordingly, one aspect of the present invention relates to a medical analysis system for pre-clinical and/or clinical analysis of data obtained from at least one patient, the system comprising:

an internal database (IDB), the database comprising a collection of data, analysis results, flow definitions, and tool definitions, and other related data for tools that utilize a database repository, a database access unit (DA), the unit being adapted for providing access to the internal database, a flow definition unit (FD), the unit providing execution of a configurable flow of analysis and visualization of a plurality of data modalities, the plurality of data modalities comprising:

a first bio-molecular modality comprising bio-molecular data related to the patient, and a second clinical modality comprising clinical data related to the patient, a tool execution engine (TEE), having an interface for the system to configure and instantiate one or more tools working on one or more of the data modalities, a tool repository, the repository comprising a collection of tools for which the system is configured to execute, said tools complying with a set of rules in order for it to be possible to visualize their execution in a graphical user interface (GUI), one or more associated external databases (EDB), the external database(s) representing data stored in the said system itself, or in a database different from the said internal database (IDB), and a graphical user interface (GUI), said interface simultaneously visualizing data, analysis results, and outcome of one or more tool executions, and wherein said interface is further adapted for simultaneously visualizing:
1) an outcome of said first bio-molecular modality, and
2) an outcome of said second clinical modality.

In one embodiment, the medical analysis system is applied to at least one patient in an in pre-clinical situation. In another embodiment, the medical analysis system is applied to a group of patients. In yet another embodiment, the medical analysis system is applied to one patient in a clinical situation. In yet another embodiment, the medical analysis system is a functioning as a clinical decision support system (CDS).

In the preclinical situation the patient data may be applied to the system to expand the data and/or for the purpose of identifying a bio-molecular or clinical signature correlating with a clinical condition in the context of cancer, cardiovascular diseases, metabolic diseases, gastro-intestinal diseases, or neurological diseases.

In one embodiment of the invention, the system of the invention is as a multimodal approach for the assisting the design of a personalized therapy.

The system provides:

A fully integrated genomic design and analysis toolbox which enables access to clinical information about the patient along with pertinent molecular information (e.g. gene expression as well as differential DNA methylation)

Integration of multiple machine learning tools specialized in a) gene expression profiling b) DNA methylation profiling c) combining clinical parameters with molecular level information d) combining with clinical, biological knowledge with molecular data d) integration of molecular modalities by statistical tools The invention allows for a configurable flow of execution of bioinformatic tools facilitating advanced means to browse the data and the results from the signature-discovery processes.

It provides a lightweight interface to a (dynamic set of) existing tools and allows them to be executed with little or no modification.

The advantage of this solution is rapid implementation and execution of analysis processes and ease of communicating methods and results clinicians and other interested parties.

Modalities

In one embodiment of the present invention, the medical analysis system according to any of the preceding claims, wherein said first bio-molecular modality and said second clinical modality is integrateable by a machine learning algorithm, the result of said integration being visualizable in the graphical user interface.

In second embodiment of the present invention, the medical analysis system according any of the preceding claims, wherein said first bio-molecular modality and said second clinical modality is integrateable by a statistical algorithm, the result of said integration being visualizable in the graphical user interface.

In a third embodiment of the present invention, The medical analysis system according any of the preceding claims, wherein said first bio-molecular modality is based on a high-throughput data sampling modality.

High-throughput analysis in the context of the present refers to the large scale analysis of biological data addressing biological or clinical questions otherwise unattainable using conventional methods at the time of filing of the present application. High-throughput is further defined by the modality generating the data for analysis.

High-throughput gene expression analysis typically involves the analysis of expression profiles comprising data of thousands expression products per sample. Gene expression data from a single microarray experiment can trace the activities of a number of genes ranging from a few thousands to hundreds of thousands under hundreds of stimuli.

High-throughput DNA methylation status profiling (such as a high-throughput differential methylation hybridization (DMH) microarray or MOMA microarray) comprising data of 100,000 s CpG sites/islands per sample.

Mass-spectrometry proteomics typically involves simultaneous measurement of 100,000 s mass-charge (m/z) values of protein peptides in a measurement setup that involves one or more mass spectrometers and additional steps to focus one particular subset of proteins in the biological sample.

Thus in one embodiment, high-throughput is defined at the range from 100,000 s to several millions such test in a single measurement (e.g. on a microarray). Specifically, gene expression data typically measures 10,000 s gene expression profiles, DNA methylation measures the methylation status of 100,000 s fragments in CpG islands, mass-spectrometry proteomics typically measures 100,000 s of m/z values.

In another embodiment, high-throughput refers to the level of distinction that would be applicable to all modalities would be their property that enables rapid simultaneous execution of millions of biochemical, genetic or pharmacological tests.

In one embodiment, the sample provided by said high-throughput data sampling modality comprise data on at least 100.000 parameter/species.

The system of the present invention enables integration of a wide range of modalities including but not limited to high-throughput modalities.

In one embodiment the first bio-molecular modality is selected from the group consisting of a high-throughput gene expression profiling, DNA methylation status profiling, comparative genomic hybridization analysis, mass-spectrometry proteomics, single nucleotide polymorphism (SNP) and other genome-wide sequencing modalities.

In another embodiment, the first bio-molecular modality is selected from the group consisting of histology modalities such as immunohistology, ELISA, enzymatic activity, PCR such as Q-PCR, RT-PCR.

In one embodiment, the second clinical modality comprising clinical data related to the patient relates to data such as age, gender, data from physical examination of the patient and other information (e.g. data from interview of patient) collected by the clinician.

Apart from the first bio-molecular modality the system enables the integration of multiple bio-molecular modalities. Thus, in a further embodiment, the flow definition unit (FD) comprises at least one further bio-molecular modality.

The additional bio-molecular modality or modalities may be any of the bio-molecular modality described herein. Thus, in one embodiment, the further bio-molecular modality is selected from the group consisting of a high-throughput gene expression profiling, DNA methylation status profiling, comparative genomic hybridization analysis, and SNP profile.

In a further embodiment, the integration of the first bio-molecular modality and said second clinical modality is integrateable based on their respective genomic annotation, wherein the result of said integration being visualizable in the graphical user interface. The genomic annotation can be gene name, function, pathway information, Gene Ontology.

Flow, States and Transactions in the System

Figure 2:
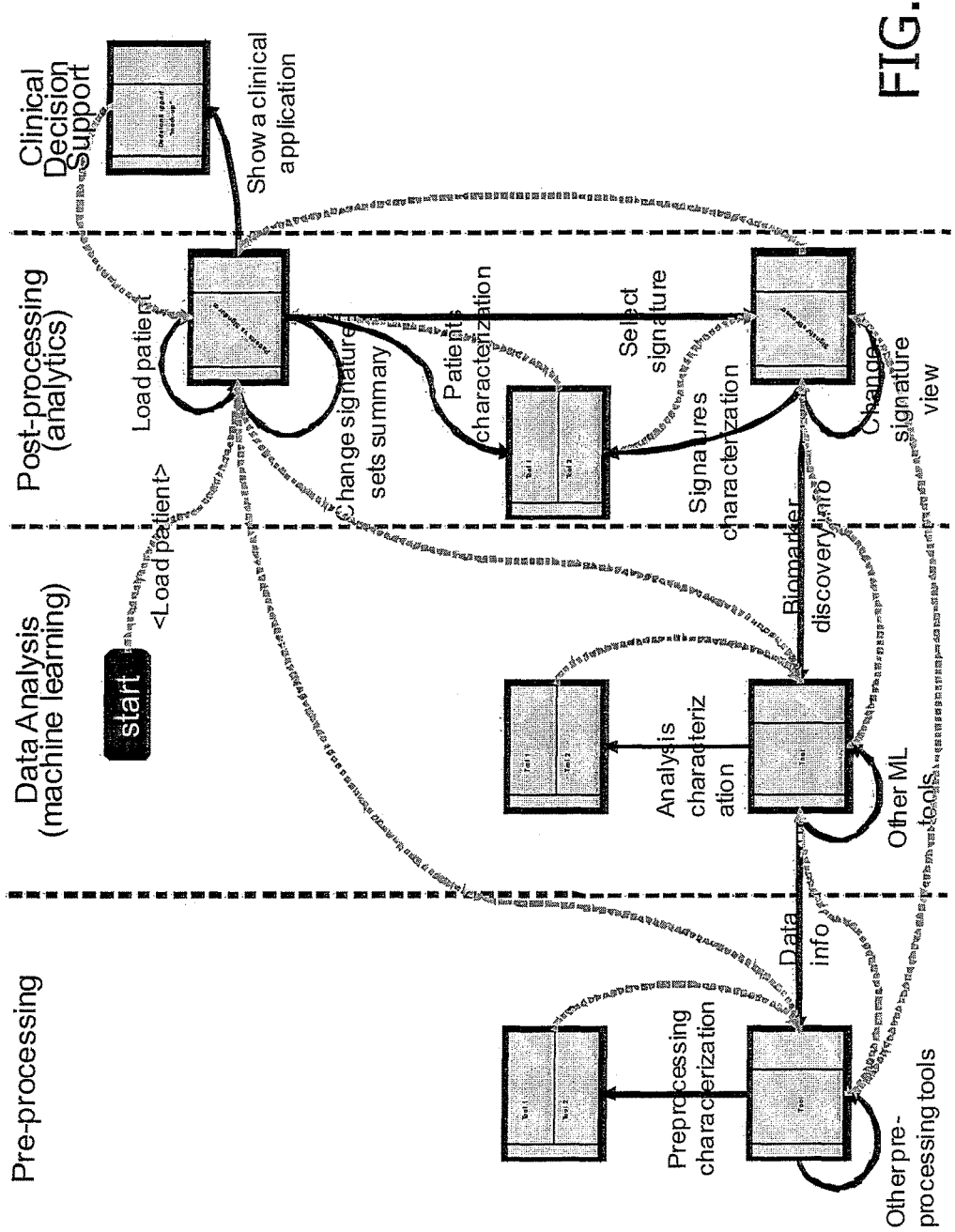
FIG. 2 shows a conceptual flow scenario for data access, analysis, and clinical decision.

A non-limiting conceptual flow scenario is provided with FIG. 2. To implement this system, in this embodiment 5 screen types defined:

A Patient Screen:
  Purpose: Demonstrate how validation patients (samples) are matched to the database of signatures.
  Data: samples (including methylation/expression profiles, and patient history, clinical indices), signatures.
  Tools: match with signatures, summary of relevant (matched) signatures.
  Control: load patient; expand a signature; select summary of signatures (e.g. gene ranks, pathways, . . . ); Decision Support.

A Signature Screen:
  Purpose: Illustrate contents and properties of a signature (optionally in the context of a sample or a set of signatures).
  Data: Signatures (set(s) of genes/loci), annotations (links to ext resources, e.g. NCBI).
  Tools: Match, summary of relevant (matched) signatures (summary of statistical data).
  Control: Navigate to "analytics" or to the earlier steps in the analysis, change view to emphasize or remove visual elements (or even change the view completely—e.g. from ordered list of genes, to heat map).

A Tool1 Versus Tool2 Screen:
  Purpose: Provide means to show output from 2 tools simultaneously with the option to "drive" tool 2 from tool 1 for comparative purposes and for multimodal data integration.
  Data: Any—depends on the tools
  Tools: Any tool.
  Example:1) tool1=hierarchical clustering vs. tool2=top down hierarchical sorting. Example 2) tool1 on gene exp data vs. tool1 on methylation data.
  Control: Provide parameters and drive tool 2. Navigate back to where called from.

Tool Screen:
  Purpose: Execute a tool within a predefined context information (e.g. current sample, current signature, current output from other tool)
  Data: Any—depends on the tools
  Tools: Any tool.
  Control: Rudimentary parameter input. Default parameters should be used and could be changed on the fly if necessary. Get some context of the flow and update context for subsequent tool calls. Navigate back to where called from. Navigate to similar tools.
  Navigate to tools that precede it in the pipeline.

A CDS Screen:
  Purpose: Visualize one or more ideas on how may the result of a match for a patient sample be translated into a CDS-like output.
  Data: Sata based on analysis and annotation
  Tools: None. Just information presented. E.g. clinical indices, therapy planning
  Control: Some data may contain hyperlinks to external sources (e.g. PubMed publications, pathway info). Navigate back to where called from.

Figure 3:
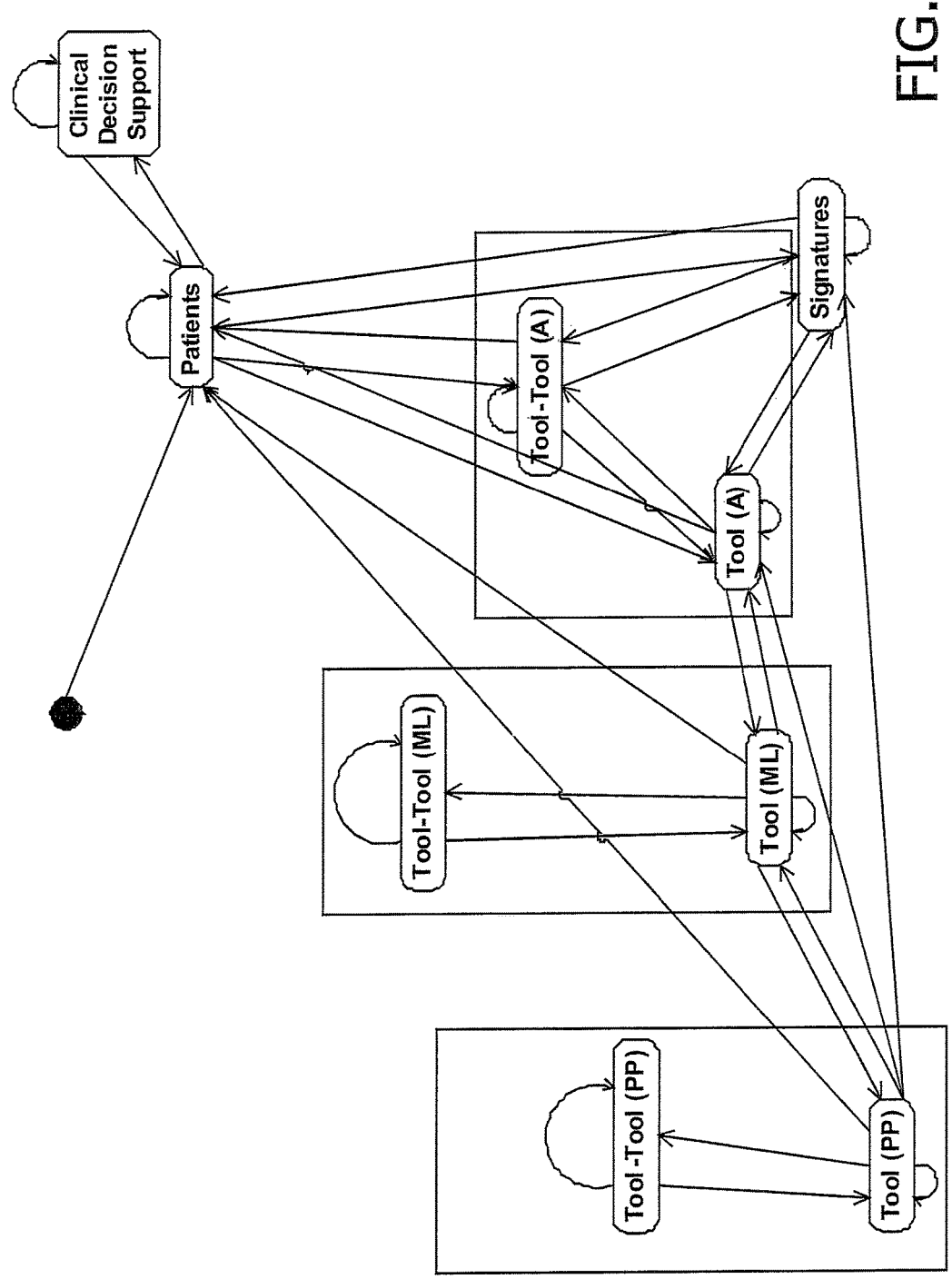
FIG. 3 shows the states of the system with respect to the analysis context and visual presentation.

In one embodiment of the present invention, the flow is defined using states and possible transitions (actions) as in the example in FIG. 3. Each state also has a screen type associated with it. To implement the allowed transitions, in this embodiment we specify:
  State from: The state originating the transition
  State to: The resulting state
  Description: free-text description of the action
  Action type: tool-call (will call an external tool); custom (will execute an internally-defined action); button (will call an external tool from a button provided on the screen)
  Tool: If applicable, a pointer to the description of the tool to be called.
  Existing constraint: The flag(s) that need to be set or unset by previous actions in order for this action to be allowed.
  Set constraint: The flag(s) that this action will set.
  Unset constraint: The flag(s) that this action will unset.

The application starts in an initial state. Upon entering a state, the application queries the transition table and compiles a subset of all possible transitions based on the state entered and the set and unset constraints in the system. The Flow Definition Unit uses this specification maintain the state of the system as the user navigates through the data and the tools.

The following data structures define the flow, the tools linked to the flow and their parameters:

Flow Definition:

| Field | Description |
| --- | --- |
| state_from | Current state |
| Type | Tool execution; internal transition; . . . |
| Description | Free-text description |
| Action | Tool name (previous slide); initialization; internal actions |
| constraint_e | User-defined variables that can be set to define constraints. For example methylation modality active vs. expression modality active; analysis mode vs. decision support mode; etc. |
| constraint_s | |
| constraint_u | |
| state_to | Next state |

Tools Definition

| Field | Description |
| --- | --- |
| Tool | Name of the actual tool |
| Number of Parameters | |
| Execution Directory | |
| Platform | <EXE, R, Matlab, Perl, Python> |
| Prepare Platform Call | e.g. load_data('file1.txt') |
| Function to Call | result = func1(par1) |
| Call prefix | result = func1(par1) |
| Call Result Variable | e.g. result |
| Tool Output type | Text or image |
| Tool Supports Split Mode | Can show result on half screen |

Tools Parameters Definitions

| Field | Description |
| --- | --- |
| Tool | Name of the actual tool |
| Parameter# | Parameter |
| Parameter type | Numeric/text/<list>/context |
| Parameter Description | Concise description in free text |
| Parameters Range | Optional; supports choice lists |
| Parameter default value | Default value |

Below a non-exhaustive list of generic tools is provided. The tools are grouped into four groups according to the application and functionality:
Pre-Processing:
i. Analysis of probe-level properties
ii. Scaling
iii. Normalization
Biomarker Discovery:
i. Feature Ranking
ii. Survival Analysis
iii. Feature Subset Selection
iv. Filters
v. Wrappers
Cross-Modal Tools:
i. Visualization of data from two or more modalities
ii. Translation from one modality to another modality
iii. Correlation of measured modalities and respective biomarkers
Clinical Decision Support Tools:
i. Signatures characterization based on one or more patient sample profiles
ii. Visualization of one or more patient profiles across multiple modalities
iii. Visualization of one or more patient profiles with respect to repertory of patient profiles.
The Application of the System The present invention combines bioinformatics software tools to be used for translational research, pre-clinical, and parts for clinical applications.

The system allows for patient-centric analysis and informatics-assisted discovery to be performed in a systematic processing pipeline that could be fine-tuned for specific clinical questions. For example, by two use scenarios of integrated analysis of multi-modality retrospective breast cancer data.

Having selected a specific patient sample, the user is presented with the basic patient-centric clinical data about the tumor, such as tumor size, stage and grade, and histo-pathological data such as hormone receptor status (estrogen receptor ER and progesterone receptor PR) and ErbB2 amplification.

Furthermore, the Clinical Data Explorer also provides access to signatures derived from high-throughput gene expression, DNA methylation and copy number measurements. New signatures can also be derived using the discovery algorithms inside PAPAyA from single or a combination of high-throughput measurements. Such signatures address different clinical needs—benign vs. malignant, tumor subtype, and relapse free survival.

From the gene expression tab in the system, the user can access the signatures derived from mRNA profiling. For example, in FIG. 10, a screenshot of the system interface when browsing a list of signatures that classify the patient as belonging to either luminal or basal subtype. Here, one of the candidate signatures is expanded to gain access to their member genes (including GIMAP6, TBCC, CRABP2 as top three genes) with access to gene cards and feature browser. One may explore one of these genes with the Feature Browser tool (cf. FIGS. 11, and 28) that plots the expression values of any given gene(s) grouped by clinical parameters. The user may observe that this gene's expression level also correlates with the hormone status (under expressed in hormone positive and over expressed in hormone positive) and tumor grade (over expressed in grade I and II, and under expressed in grade III). This tool thus enables the user to gain insights into clinical associations that were not used in the signature discovery process. This can be used to establish the significance of the genes as well as confidence in the signatures in which these genes are found.

Figure 13:
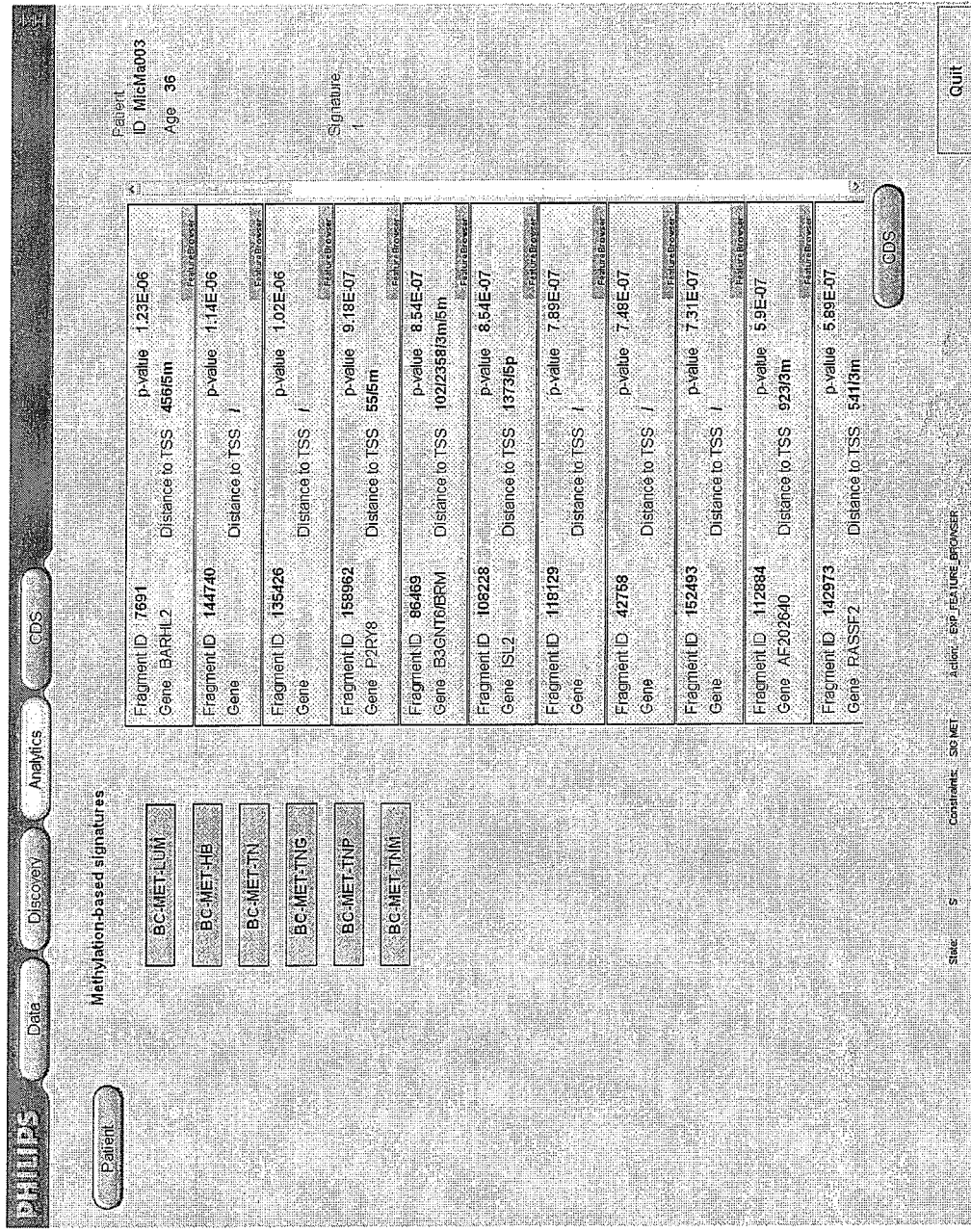
FIG. 13 shows an example of a screen related to exploration of the DNA methylation signatures.
Figure 14:
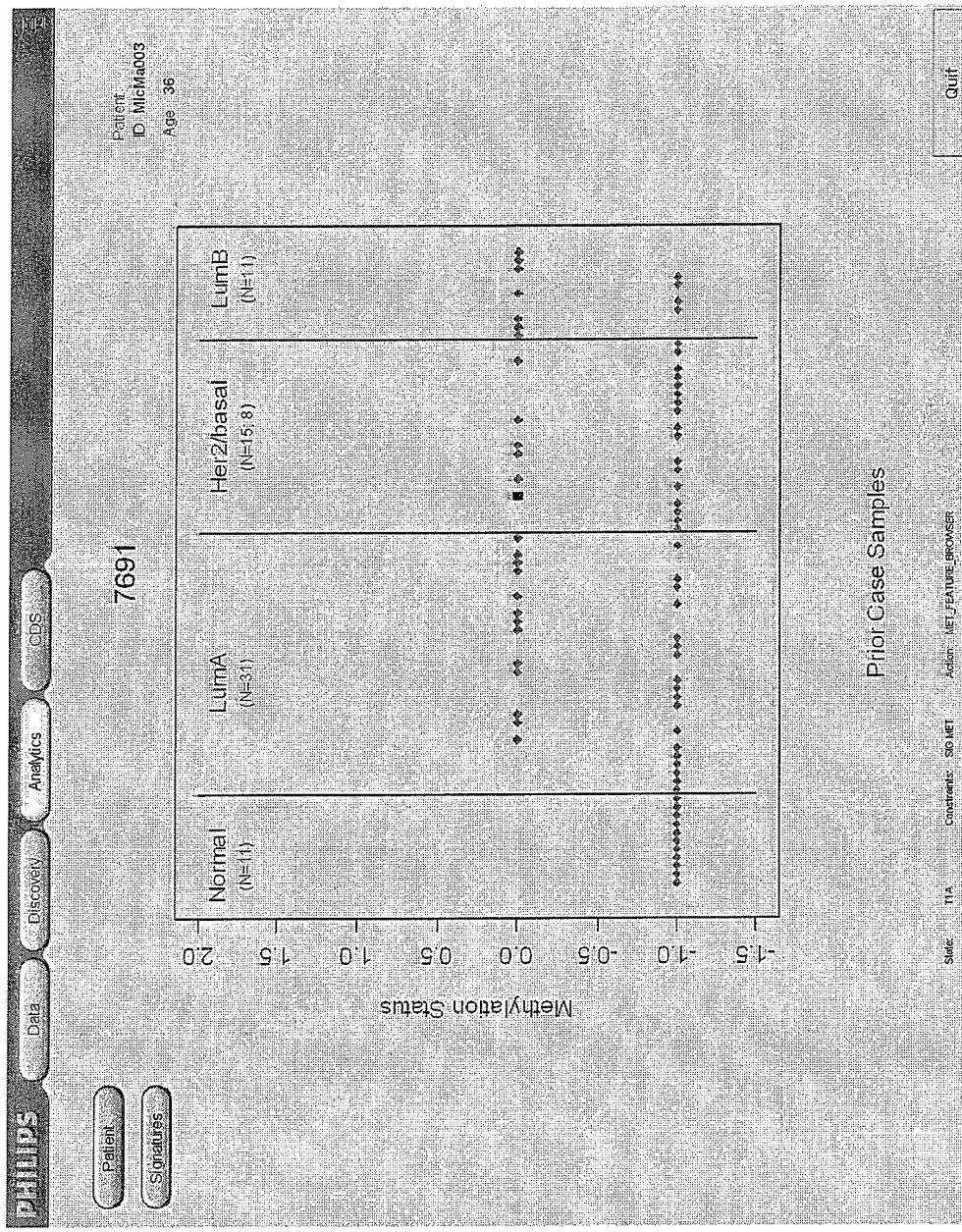
FIG. 14 shows an example of a feature-browser for DNA methylation markers.
Figure 15:
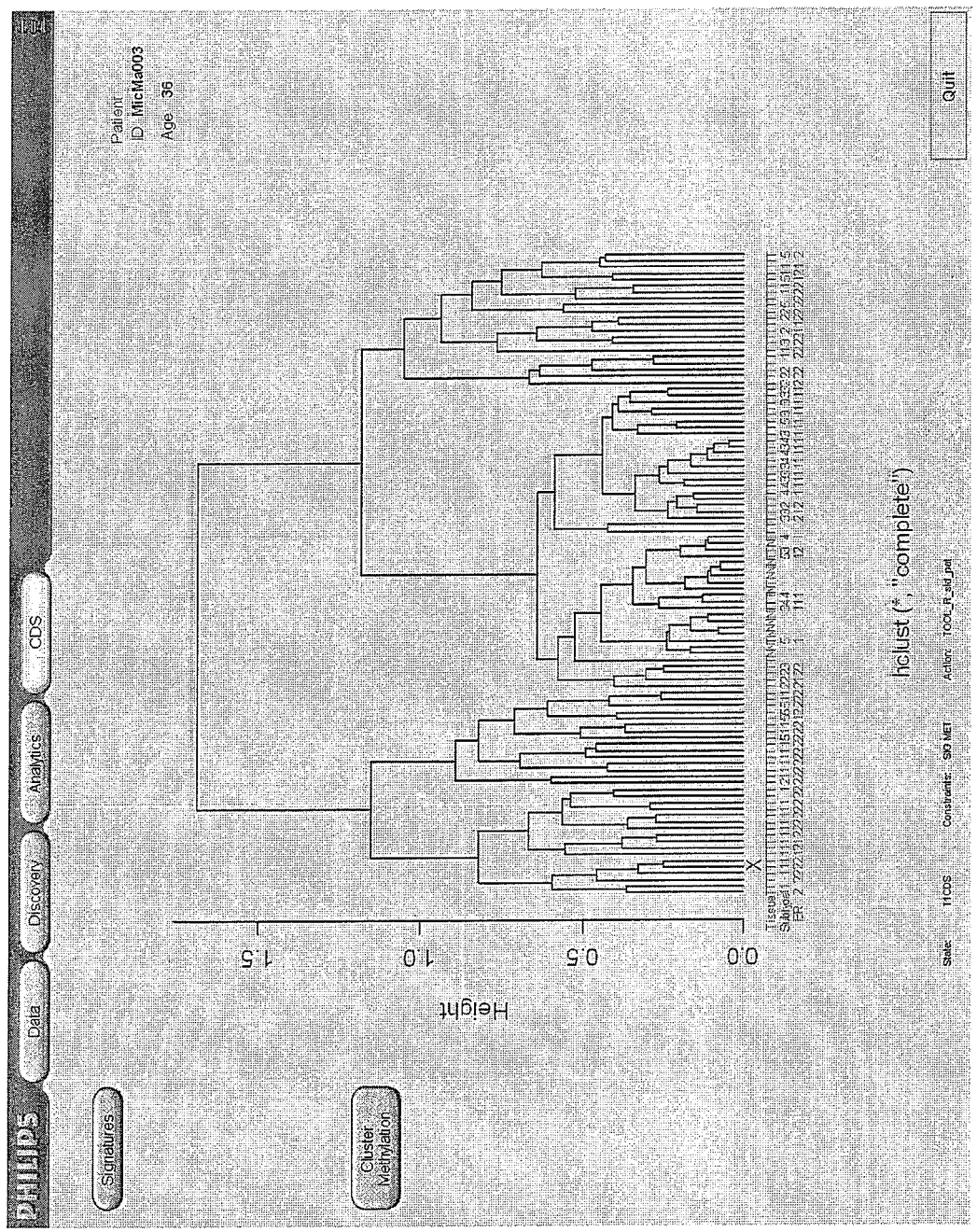
FIG. 15 shows an example of a clinical decision support (CDS) screen for the methylation Signature

In another use scenario, the system is used to explore molecular signatures based on DNA methylation microarray measurements (cf. FIG. 13). To assess the signatures, a different tool is used, which visualizes the methylation states for specific loci in the genome (cf. FIG. 14).

Accordingly one aspect of the present invention relates to a process for the discovery of bio-molecular or clinical signature associated with a specific clinical condition comprising the use of the medical analysis system according to any of the preceding claims.

The data may be obtained from a patient suffering from any clinical condition. In one embodiment of the present invention, the patient has a clinical condition selected from the group consisting cancer, a cardiovascular disease, a metabolic disease, a gastro-intestinal disease, a neurological disease.

The bio-molecular or clinical signatures discovered by the system may be applied to the clinic eg. for the stratification of patients in clinical conditions.

In one embodiment, the clinical condition is selected from the group consisting of cancer, a cardiovascular disease, a metabolic disease, a gastro-intestinal disease, a neurological disease. In a particular embodiment, the cancer is breast cancer or colon cancer.

The signature may relate to any of the modalities or combinations of any modalities employed by the systems of the invention.

Thus, in one embodiment, the signature is a gene expression signature, DNA methylation status signature, comparative genomic hybridization signature and SNP signature.

In one embodiment, the system provides means of analysis complex data obtained from molecular diagnostic and monitoring tests. These targeted tests provide a molecular view of the progress of a patient's disease right from the point of diagnosis, to treatment planning, to follow up of treatment.

In another embodiment, the system of the invention may be used to develop decision support systems that aid the clinicians throughout the whole care cycle. These systems provide a comprehensive view by combining the discovered molecular signatures with the imaging and treatment planning information. These systems can suggest therapy choices (e.g. hormone or chemotherapy) and the appropriate image modalities for monitoring the progress of the disease.

In a third embodiment, the system is used to provide molecular information packages (e.g. molecular signatures with associated meta data) to the clinicians or to third party decision support systems.

In yet an embodiment, the system is used to develop enhanced clinical guidelines that can be customized to a patient's molecular profile. Such guidelines may be useful in molecular medicine.

The inventor further provide the for use in a clinical setting in a completely different way—therefore the inventors have provided different ways to explore and present the data thus allowing for clinical decision support (CDS) to be applied to patient data. The CDS part of PAPAyA assists in the interpretation of the patient's tumor profile. It provides a personalized view with respect to the selected signature.

Signatures that are derived from the discovery process are eventually applied to stratify the patient samples and can be used to assign confidence in a stratification based on the signature's performance with respect to all patients in the database. Currently the PAPAyA system's CDS modules include Support Vector Machine based classifiers for predicting tumor subtype using gene expression or methylation profiling data. These statistics could provide the clinician with the insights to tailor the treatment to the physiological state of the patient. Breast cancer clinical prognostic indices such as Nottingham Prognostic Index and St. Gallen Consensus can also be easily incorporated into patient assessment. Additionally the architecture allows for integration of third party signatures into the system.

A further aspect of the present invention relates to a process for clinical decision support comprising the use of the medical analysis system according to any of the preceding claims.

The process reflects the continuation of the signature discovery process into the application of the system and the signature in a clinical application.

Thus in one embodiment, the data of a patient is applied to the system for identification of a bio-molecular or clinical signature associated with a clinical condition.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Figure 4:
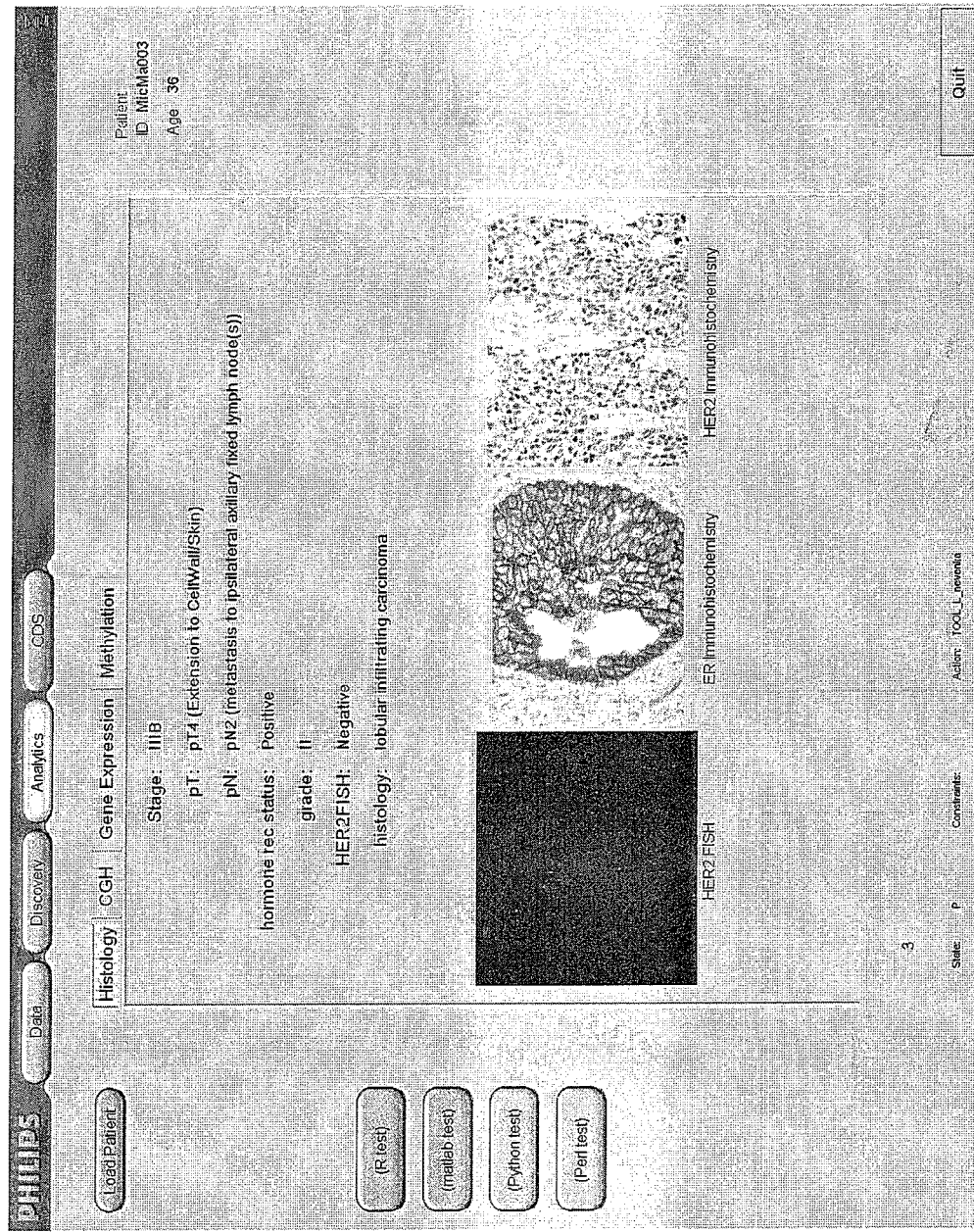
FIG. 4 shows an example of the main screen of the system of the invention.

The application opens with the Analytics screen with a default patient loaded (FIG. 4). The user can load patient information from this screen and begin the different kinds of analyses provided in the Genomic Design and Analysis Toolbox (GDAT). The first modality that is shown is Histology, where you can see the summary of the histopathological analysis performed on the patient sample.

Loading Patient Information from the Database

Figure 5:
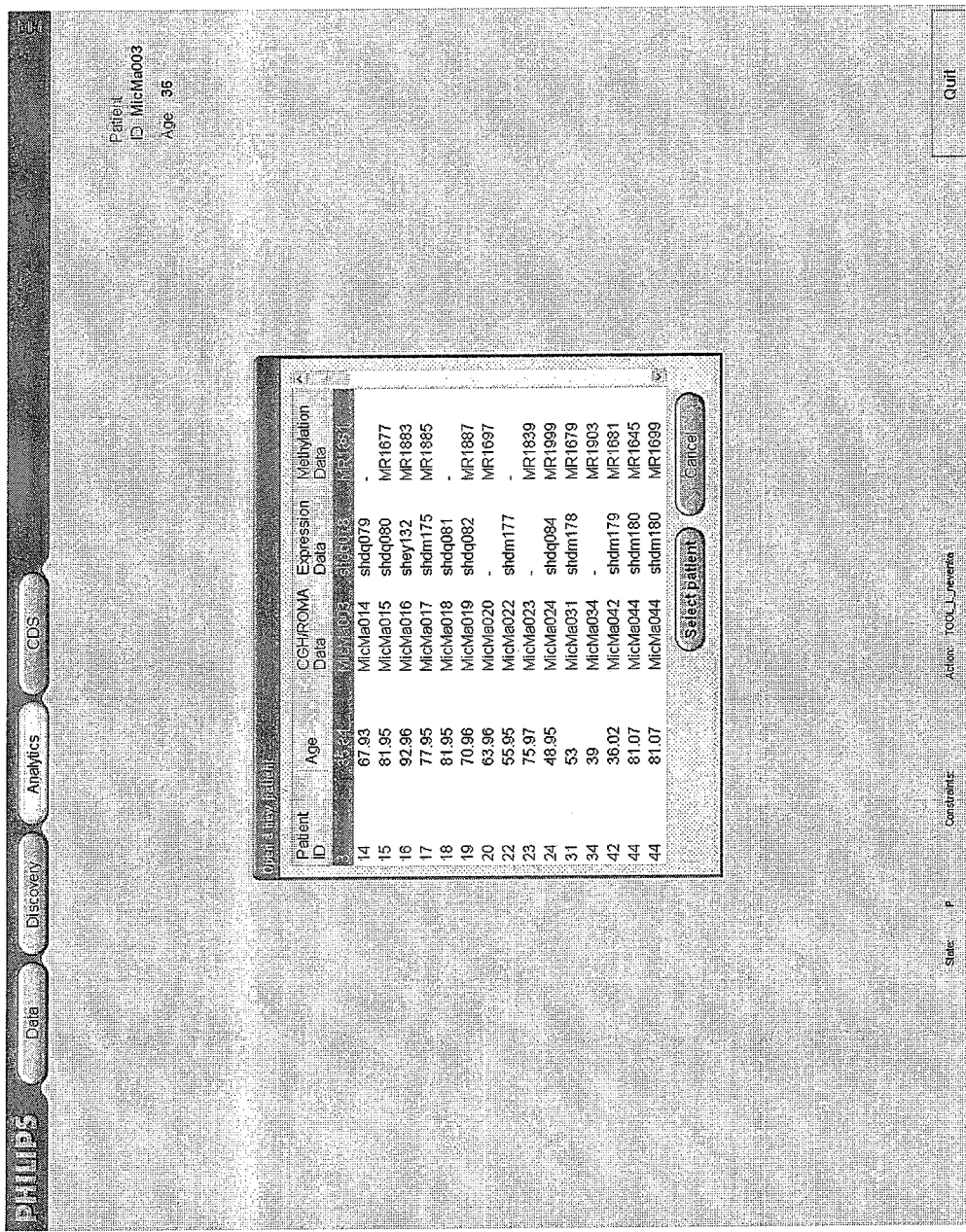
FIG. 5 shows an example of loading patient information from the database.

Summarized patient (samples) information from the database is shown and the application allows selection (highlighting) of a patient for further analysis (FIG. 5).

Example 2

The Histopathological Modality

Figure 6:
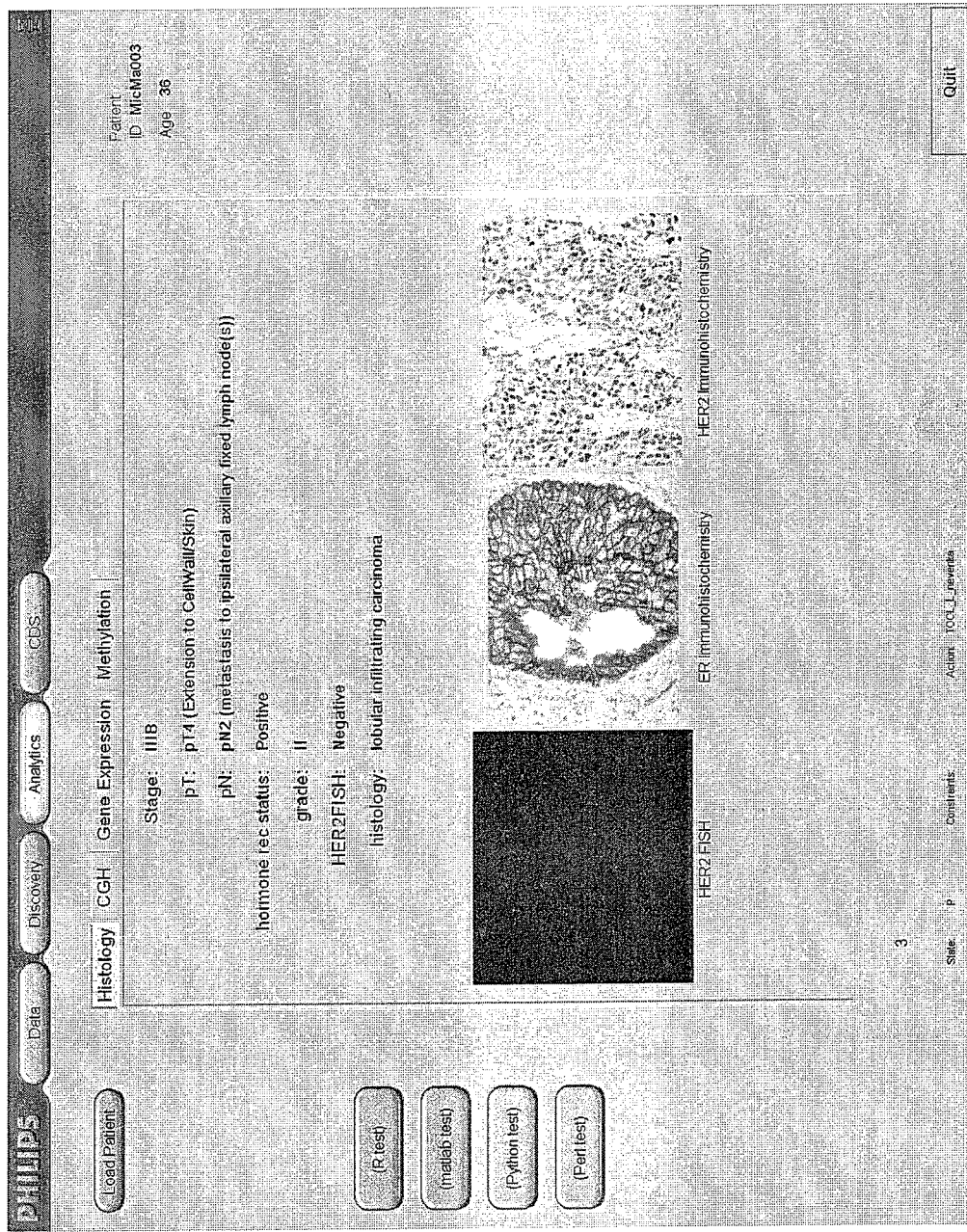
FIG. 6 shows an example of a screen related to the histopathological modality.

Summary of the histo-pathological analysis for a given patient is shown in this screen including status of Estrogen Receptor, Progesteror Receptor, Her2 overexpression by FISH and immunohistochemistry (FIG. 6).

Example 3

The CGH Modality

Figure 7:
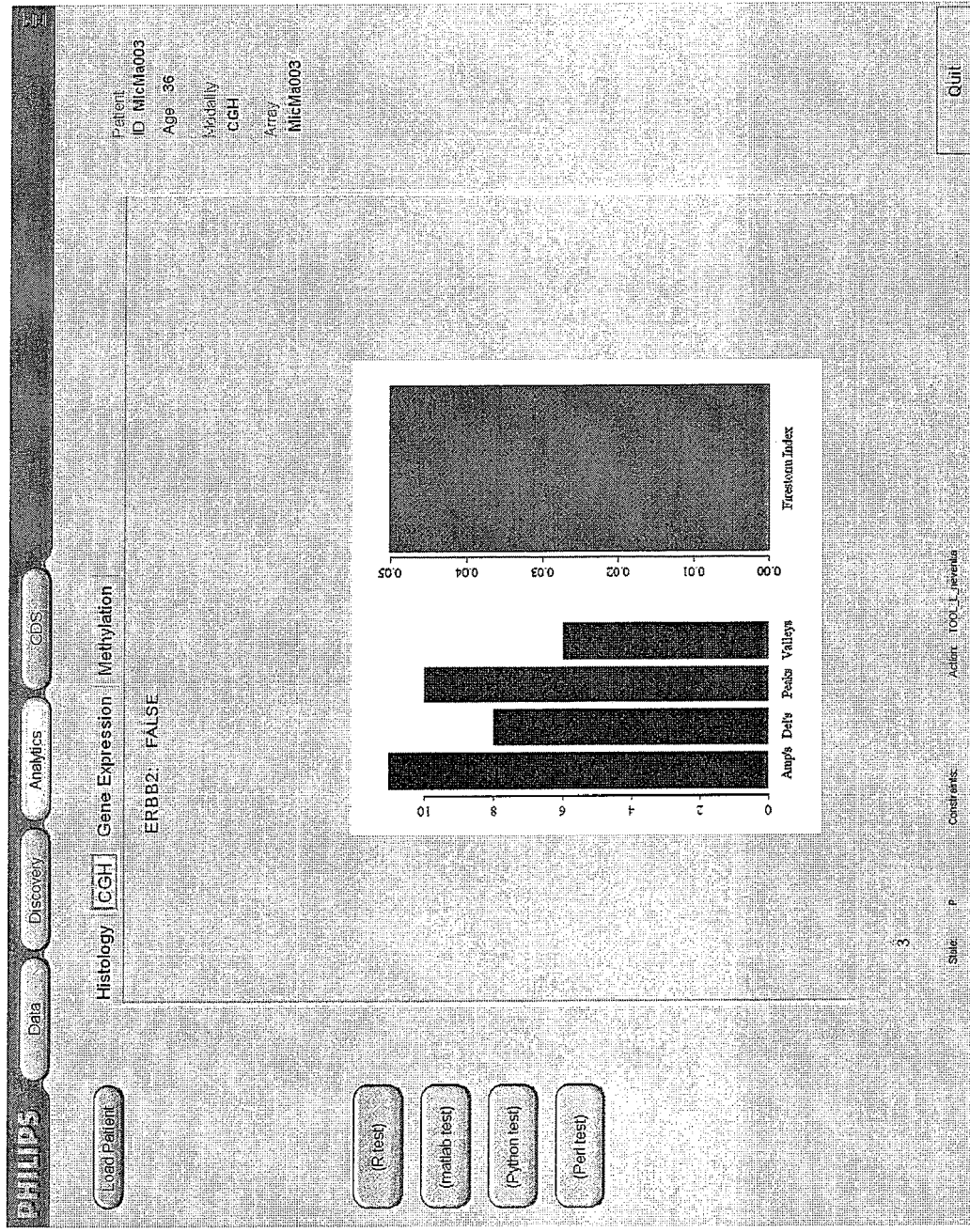
FIG. 7 shows an example of a screen related to the comparative genomic hybridization (CGH) modality.

Summary of the Comparative Genomic Hybridization (CGH) data associated with the sample, such as number of gene amplifications, deletions, etc., along with the Firestorm index for the sample from ROMA data (Representational Oligonucleotide Microarray Analysis). Cf FIG. 7.

Example 4

The Gene Expression Modality

Figure 8:
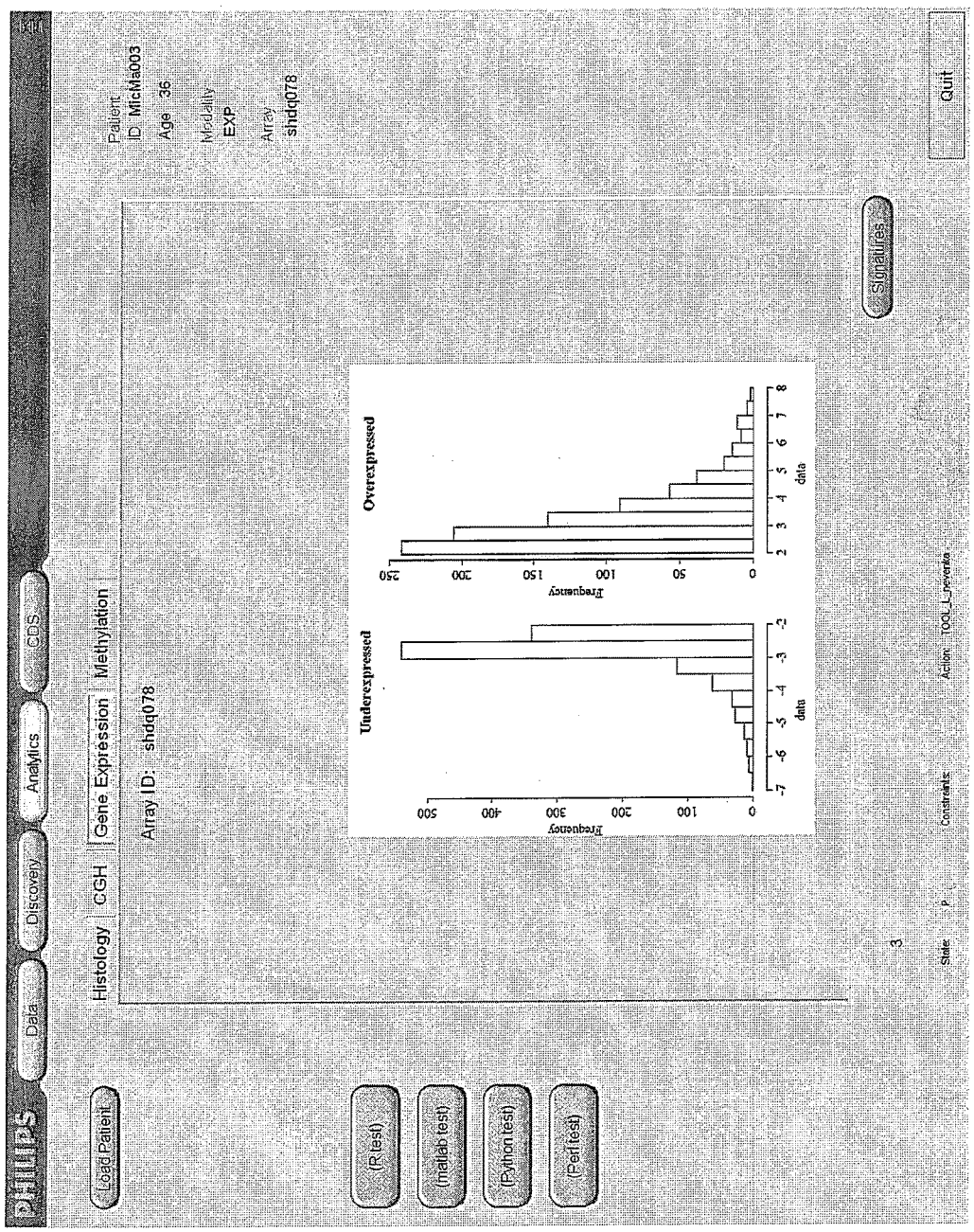
FIG. 8 shows an example of a screen related to the gene expression modality.

Summary of the gene expression data for the sample, allowing further exploration of the gene expression signatures etc. (cf. FIG. 8).

Example 5

Figure 9:
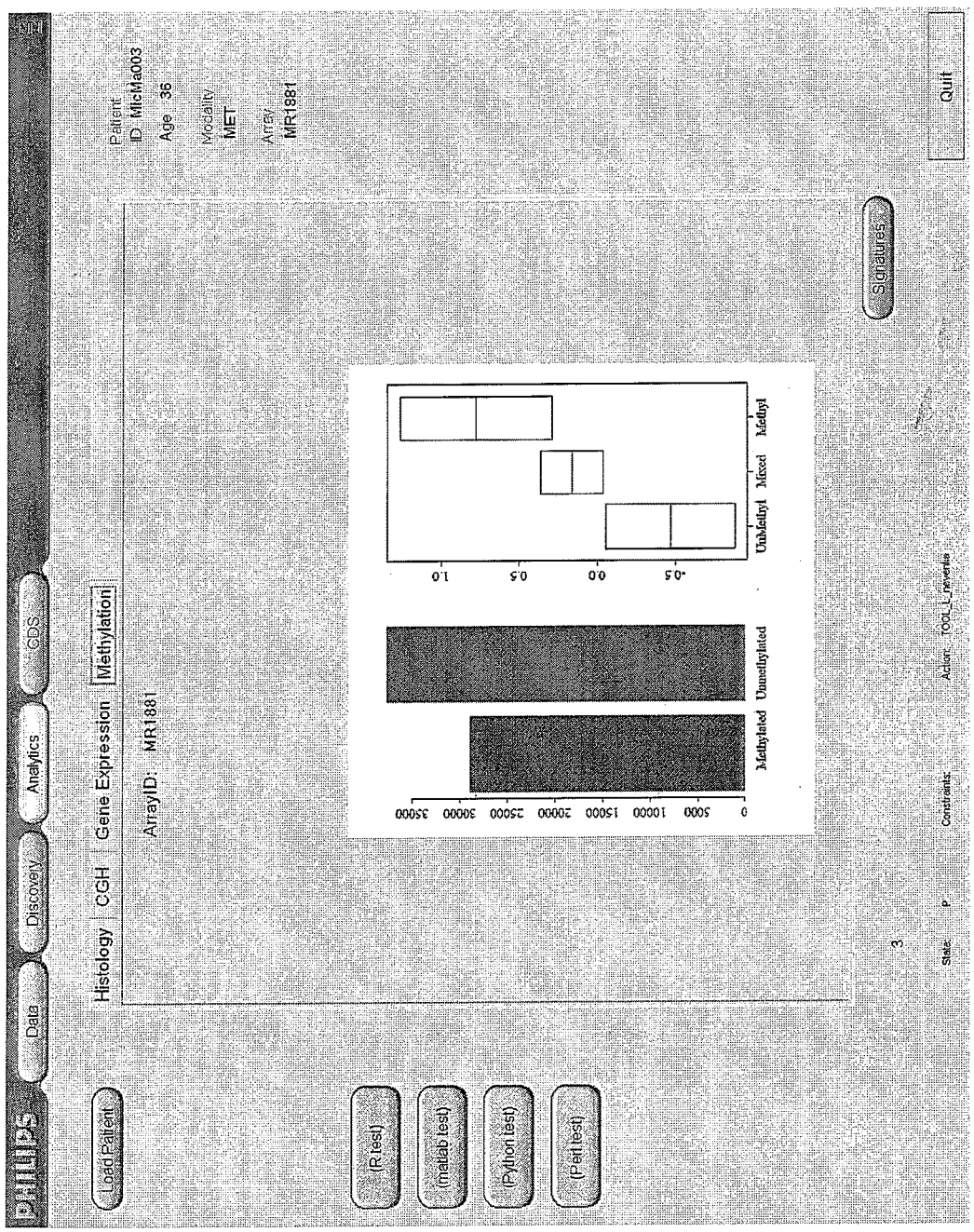
FIG. 9 shows an example of a screen related to the DNA methylation modality

Summary of the differential methylation data obtained by Methylation Oligonucleotide Microarray Analysis (MOMA) for the sample is shown. This also allows further exploration of potential methylation-based signatures (cf. FIG. 9).

Example 6

Exploring the Gene Expression Signatures

Figure 10:
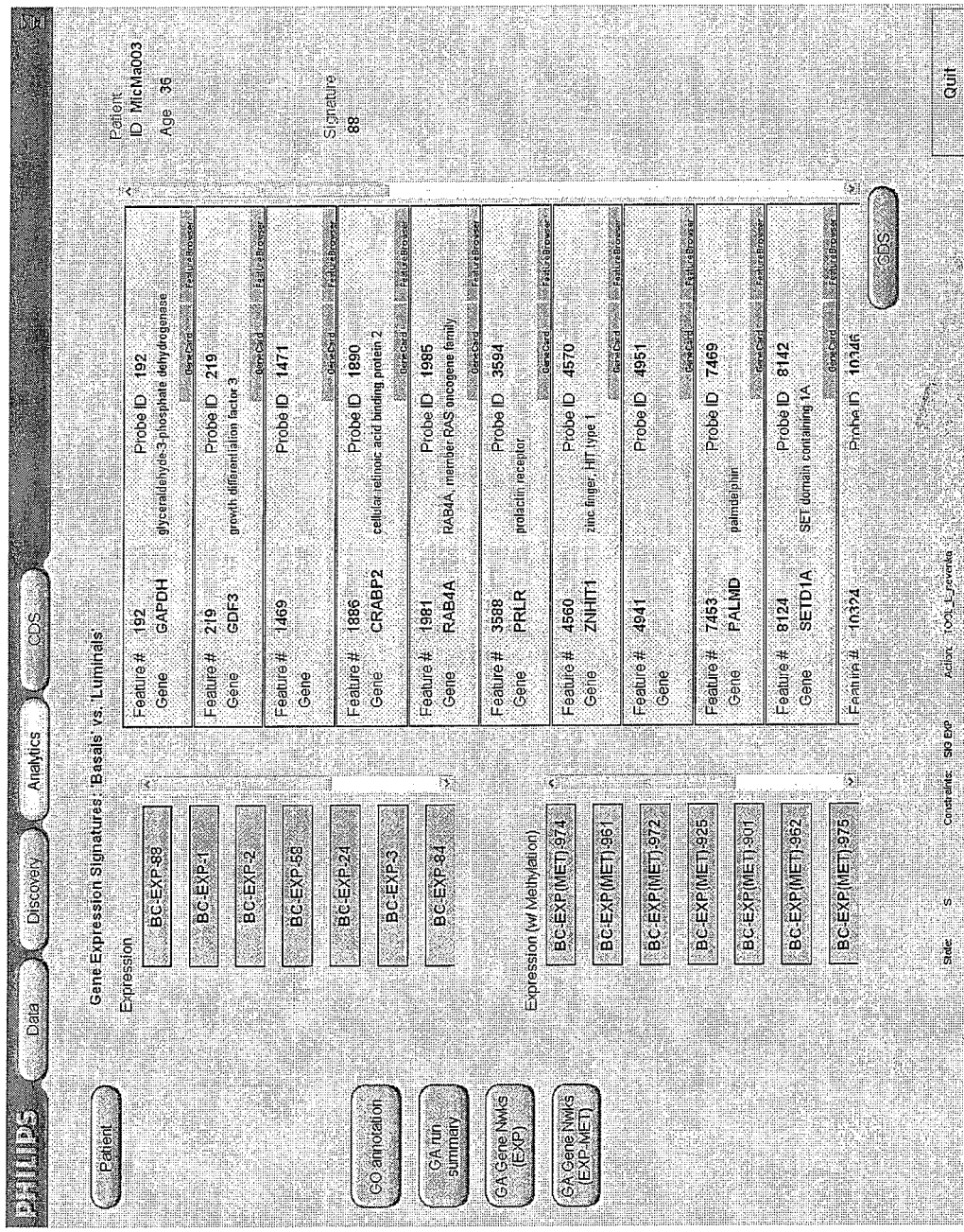
FIG. 10 shows an example of a screen related to exploration of two groups of gene expression signatures, one using solely gene expression data, and another using gene expression data in conjunction with DNA methylation data.

This screen can be reached by clicking on the "Signatures" button at the bottom right hand corner of the Gene Expression modality screen (cf. FIG. 10). Signatures identified by using gene-expression data alone as well as signatures discovered using gene expression and methylation data analysis are shown. The top signatures ranked according to their statistical relevance to the particular patient are shown. Clicking on any of the signatures on the left-hand side of the screen provides a summary of all the genes included in the signature. There are links to external sources of data for the individual genes such as "FeatureBrowser" and "Genecard".

Example 7

The FeatureBrowser for Gene Expression Signatures

Figure 11:
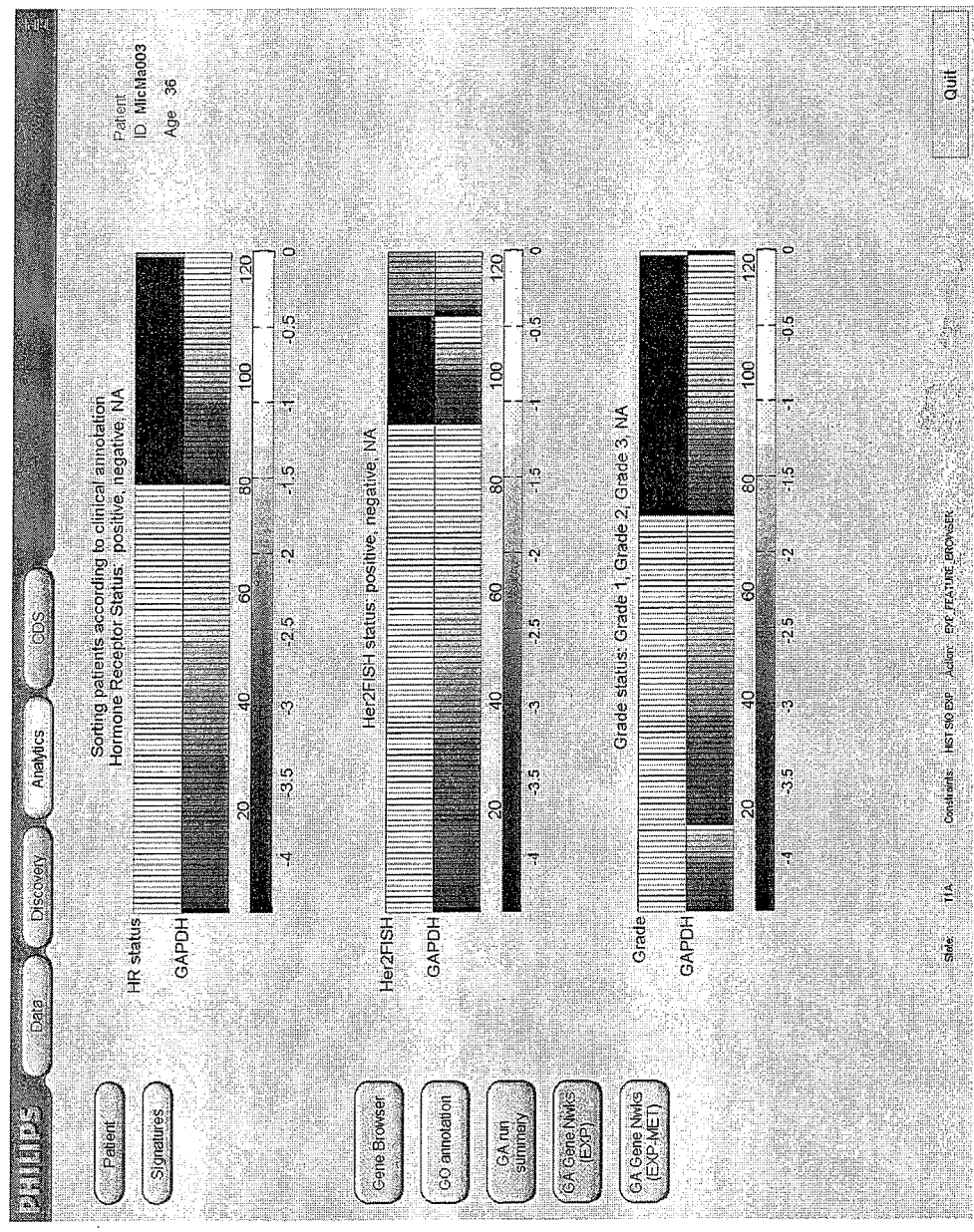
FIG. 11 shows an example of a feature-browser for gene expression signatures.

When the FeatureBrowser is called (clicked on) for a particular gene, this tool shows the distribution of the gene's expression levels across all the patients sorted according to different clinical annotations such as hormone receptor (HR) status, Her2FISH status and tumor grade status (cf. FIG. 11).

Example 8

The Genecard Link for Gene Expression Signatures

Figure 12:
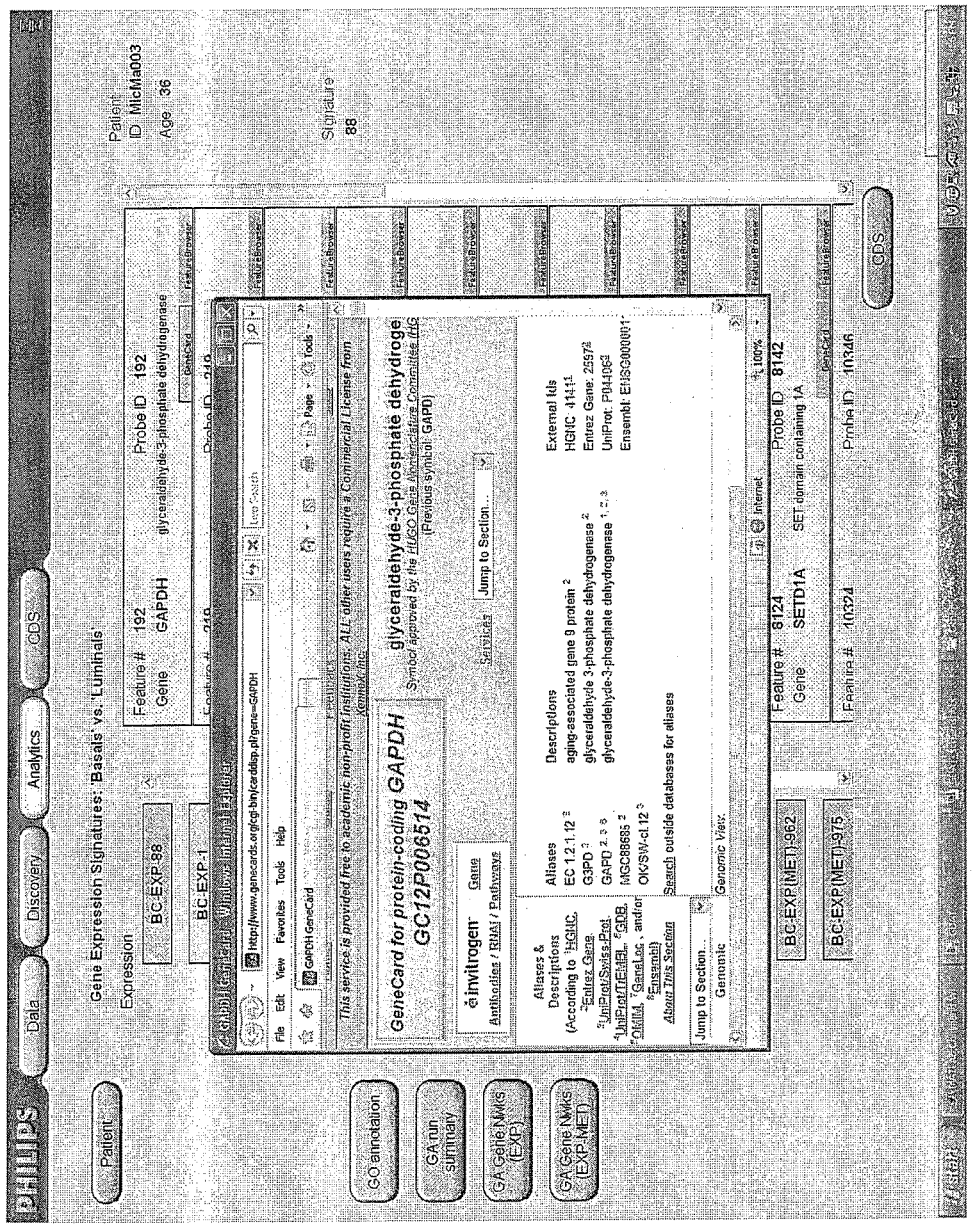
FIG. 12 shows an example of a Genecard link for gene expression signatures.

Clicking on the "Genecard" link for any given gene, opens up an Internet browser that allows the user to get publicly-available information about the gene from external resources (cf. FIG. 12).

Example 9

Exploring the Methylation Signatures

Similar to the gene expression signatures, the user can choose to explore the DNA Methylation signatures within the Methylation modality. This also allows for further exploration of the methylation markers using the FeatureBrowser links (cf. FIGS. 13 and 14).

The CDS Screen for the Methylation Signature

In this screen (cf. FIG. 14), the methylation signatures are used to cluster the patients, with the current patient being marked by an 'X' mark in the figure. This allows the user to view the patient's clinical annotation based on the patient's methylation profile.

The "Cluster Methylation" button on the left allows the user to cluster the patients according to any of the methylation signatures, thus providing access to many different clustering outputs similar to the one shown here.

Example 10

The Discovery Section

The discovery section provides access to many of the discovery tools that were used in generating the signatures. Here we include statistical methods and public as well as proprietary machine learning algorithms. The individual tools can be access using the buttons on the left (cf. FIG. 16).

Example 11

The Genetic Algorithm Summary Tool

Figure 16:
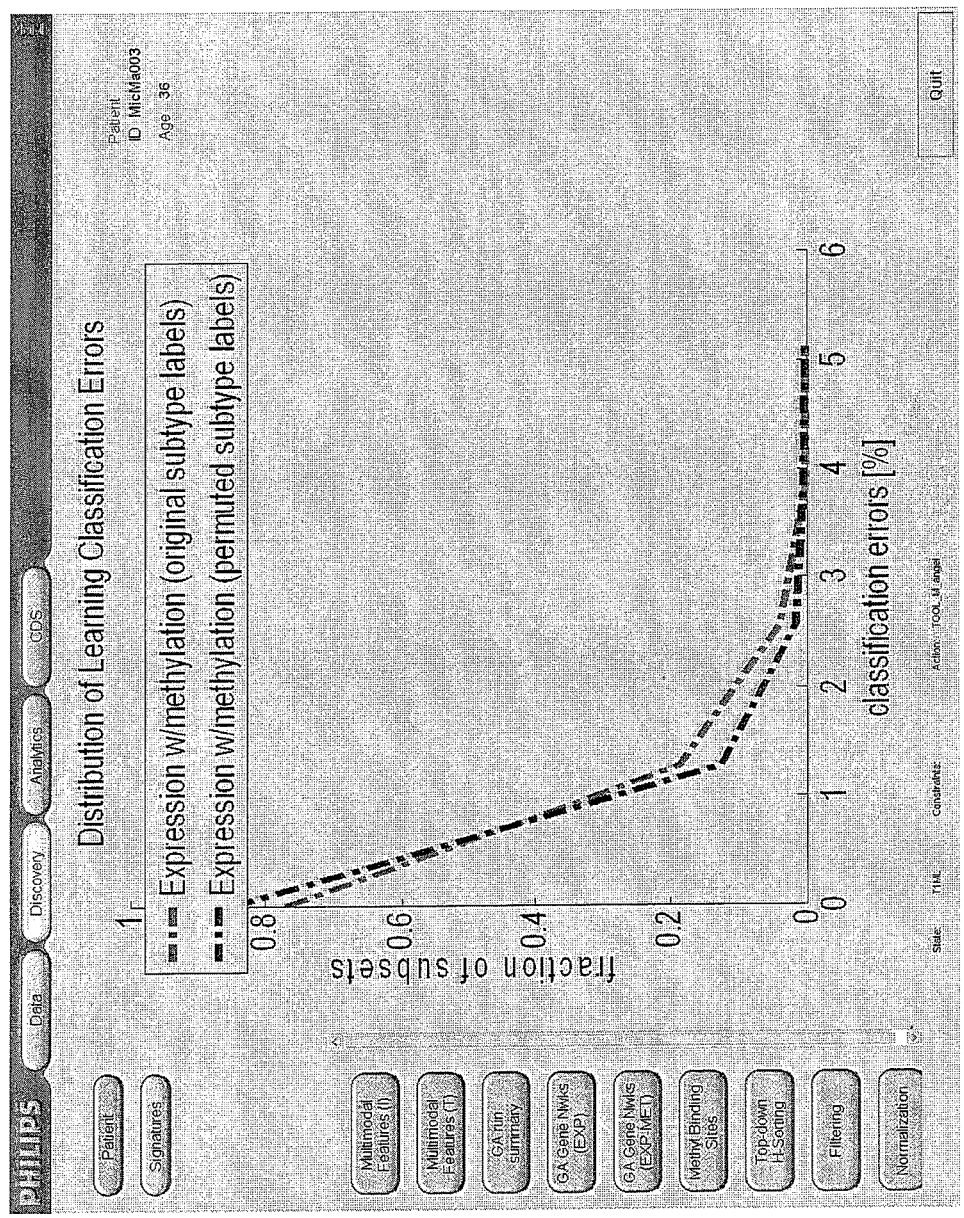
FIG. 16 shows an example of a screen related to the genetic algorithm summary tool.
Figure 17:
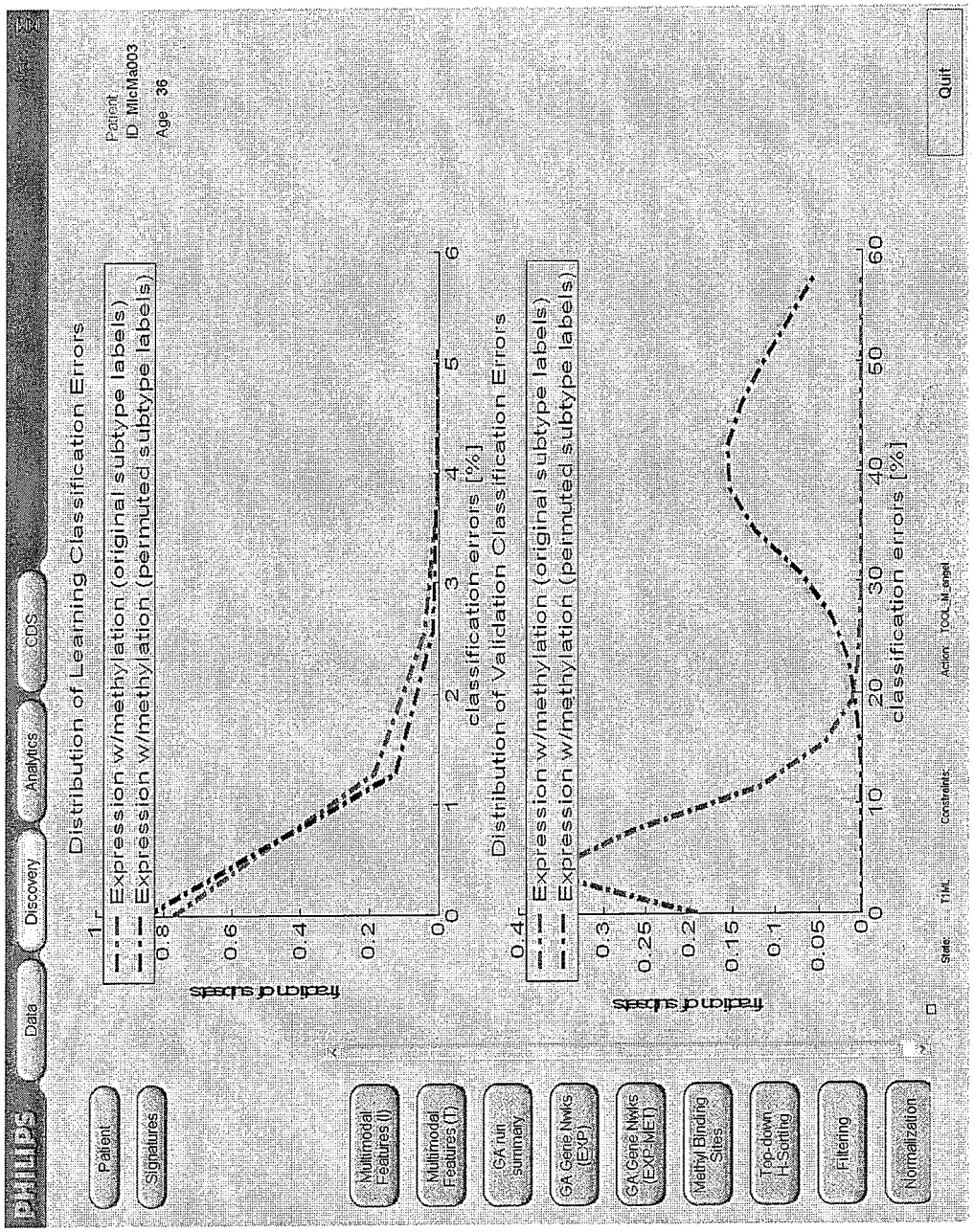
FIG. 17 shows an example of a split-screen related to compression of the output of two genetic algorithm summary tools.

This tool displays a summary of the learning and validation performance of the genetic algorithm-based signature discovery tool. The tool can be used to display the learning and performance on individual screens or as a split-screen, as shown in FIGS. 16 and 17.

Example 12

The Gene Co-Occurrence Tool

Figure 18:
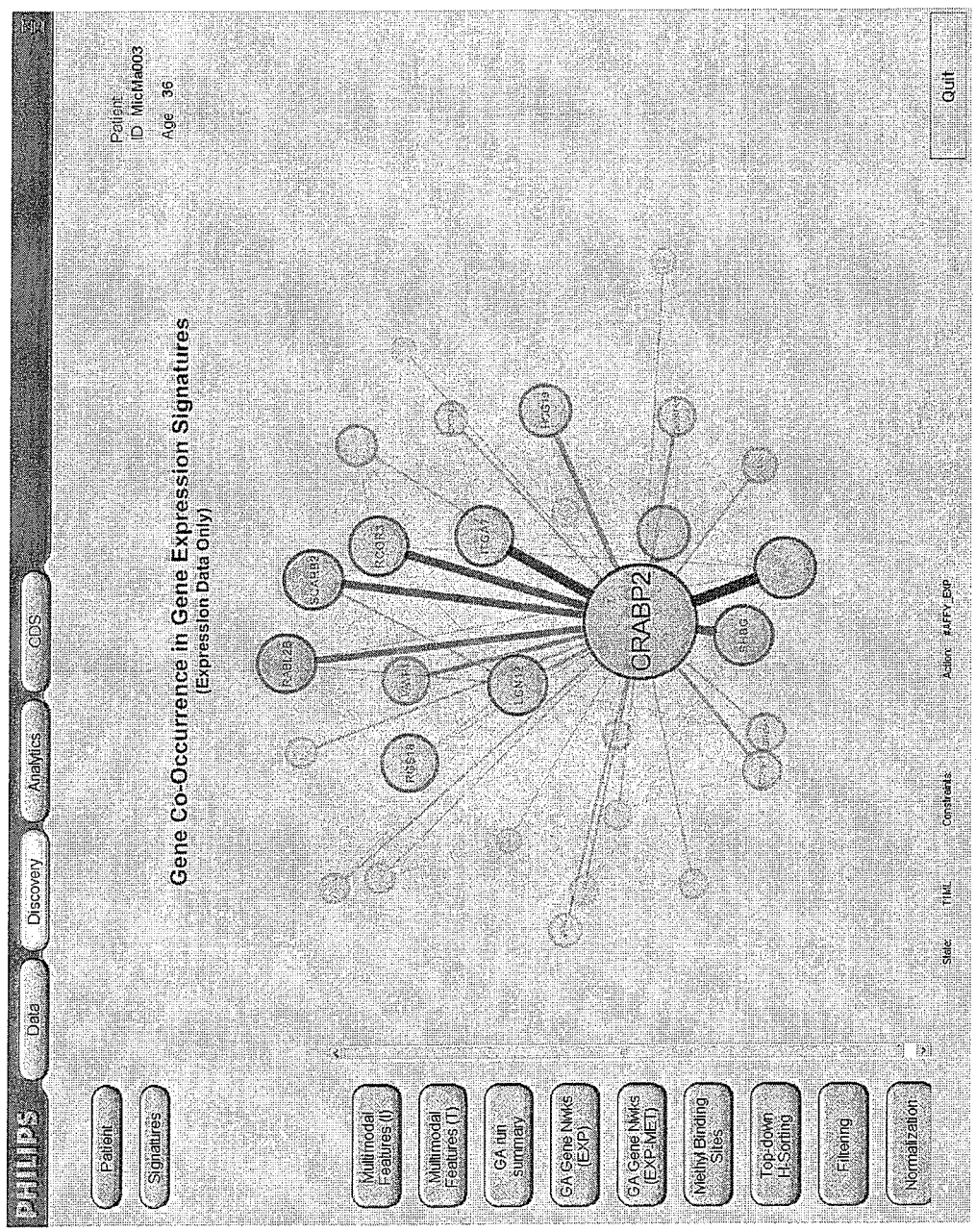
FIG. 18 shows an example of a screen related to the gene co-occurrence tool.

This tool displays the gene co-occurrence within the signatures discovered by the genetic algorithm. The tool can be used to look at the gene co-occurrence for signatures that were discovered using gene expression data alone by clicking on the "GA Gene Nwks (EXP)" button OR the signatures discovered by exploiting both gene expression and methylation data using the "GA Gene Nwks (EXP-MET)" button (cf. FIG. 18).

Example 13

The Methyl Binding Sites Tool

Figure 19:
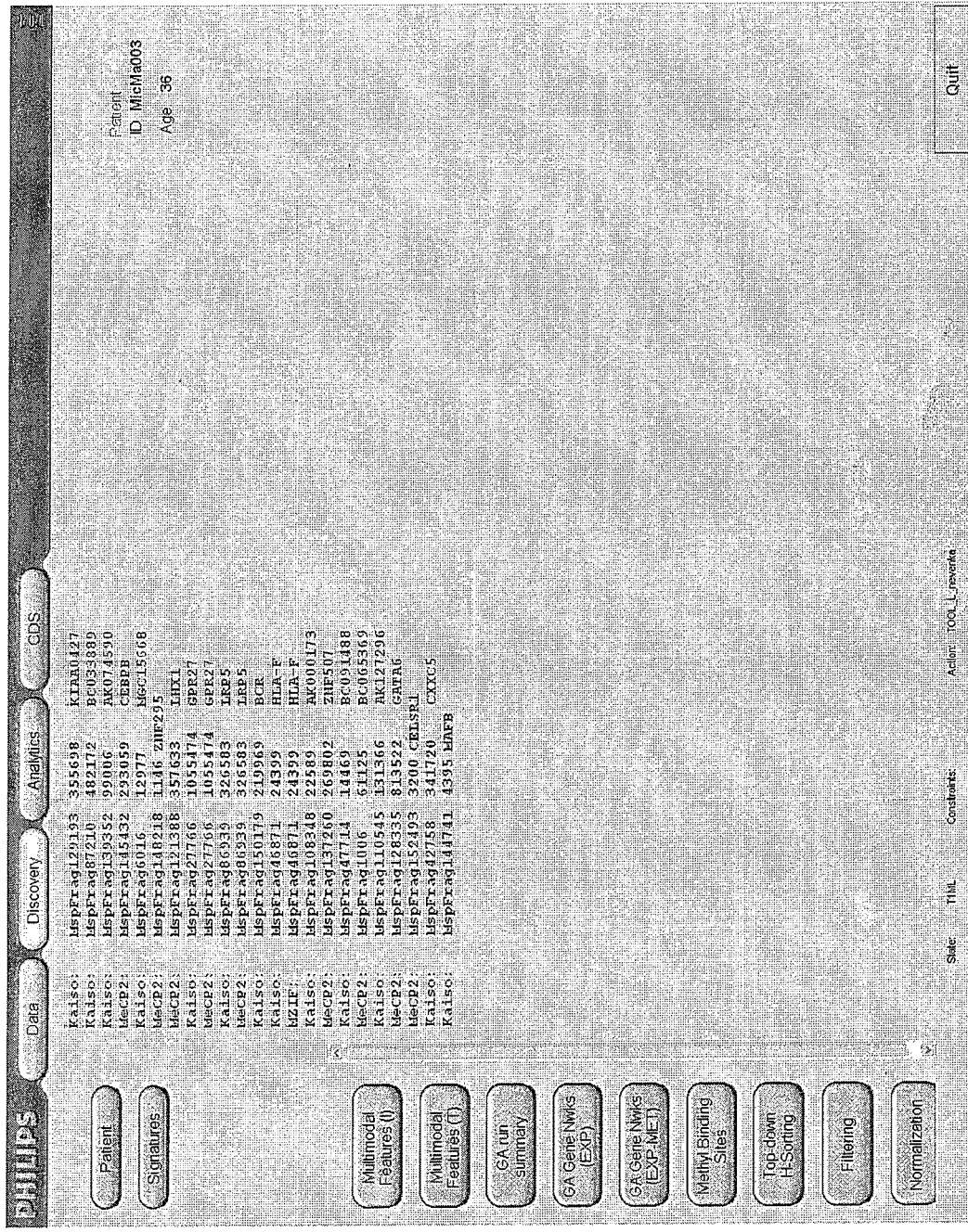
FIG. 19 shows an example of a screen related to the methyl binding sites tool.

This tool shows relevant methyl binding sites for the significant differential methylation probes (sequences), see FIG. 19.

Example 14

The Top-Down Hierarchical Sorting Tool

Figure 20:
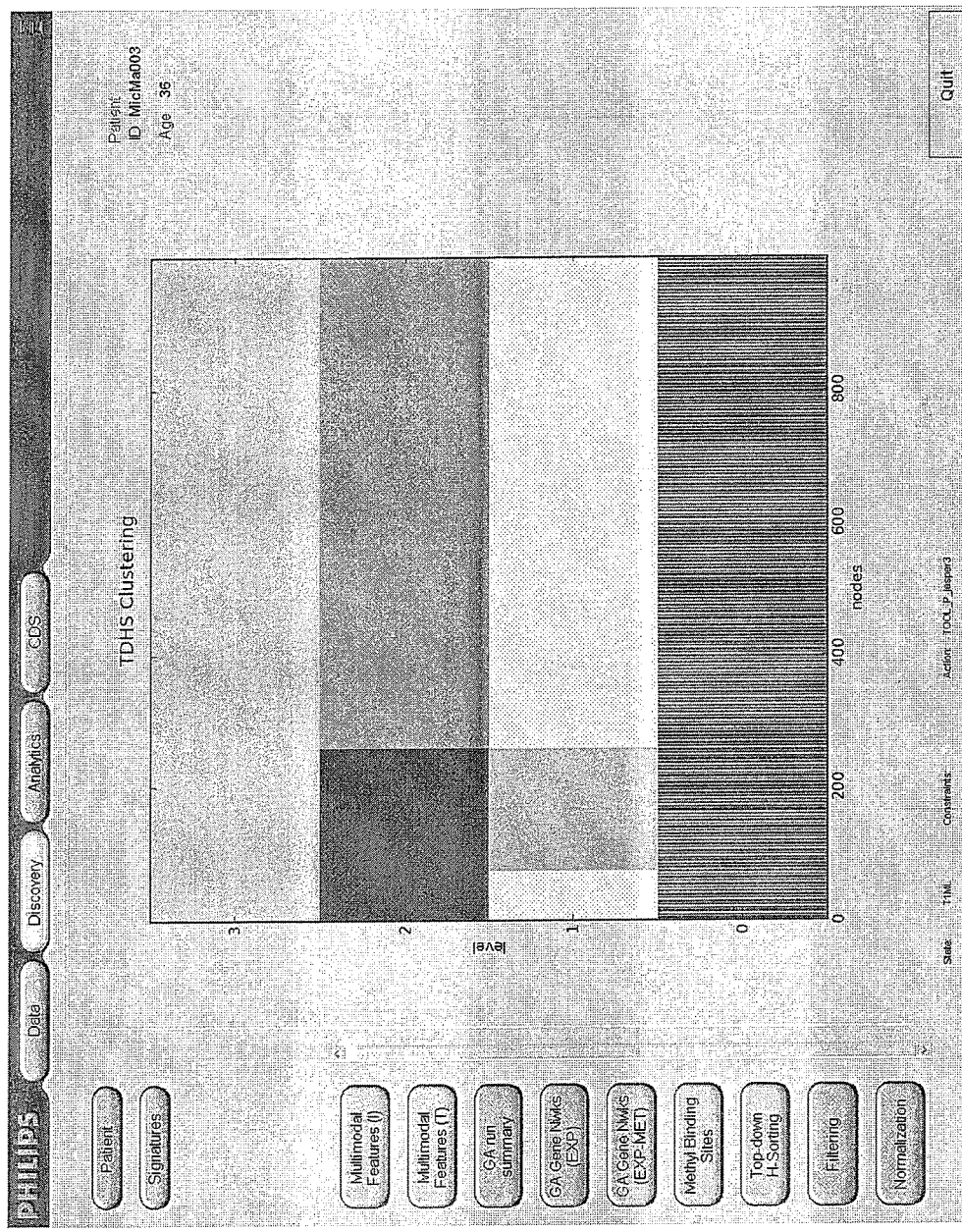
FIG. 20 shows an example of a screen related to top down hierarchical sorting (TDHS).

Top down hierarchical sorting (TDHS) is similar to a clustering algorithm except it performs sorting of the most similar patterns (where local match is high) as opposed to hierarchical clustering where the two patterns show global similarity (cf. FIG. 20).

Example 15

The Gene Expression Filtering Tool

Figure 21:
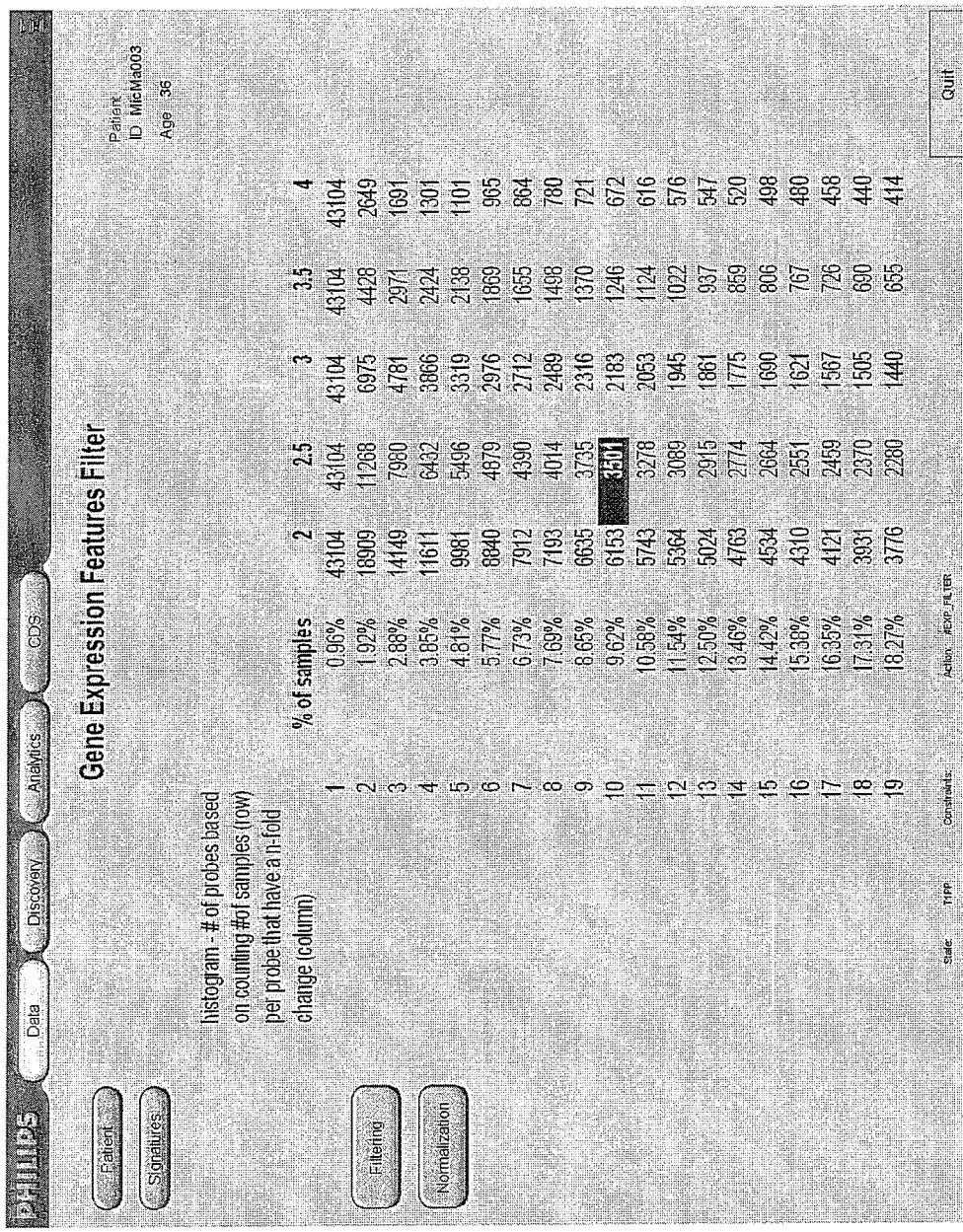
FIG. 21 shows an example of a screen related to the gene expression filtering tool.

This tool allows the user to filter the gene expression data based on n-fold expression intensity change (cf. FIG. 21).

Example 16

Multimodal Correlation Feature Analysis—Graphics Output

Figure 22:
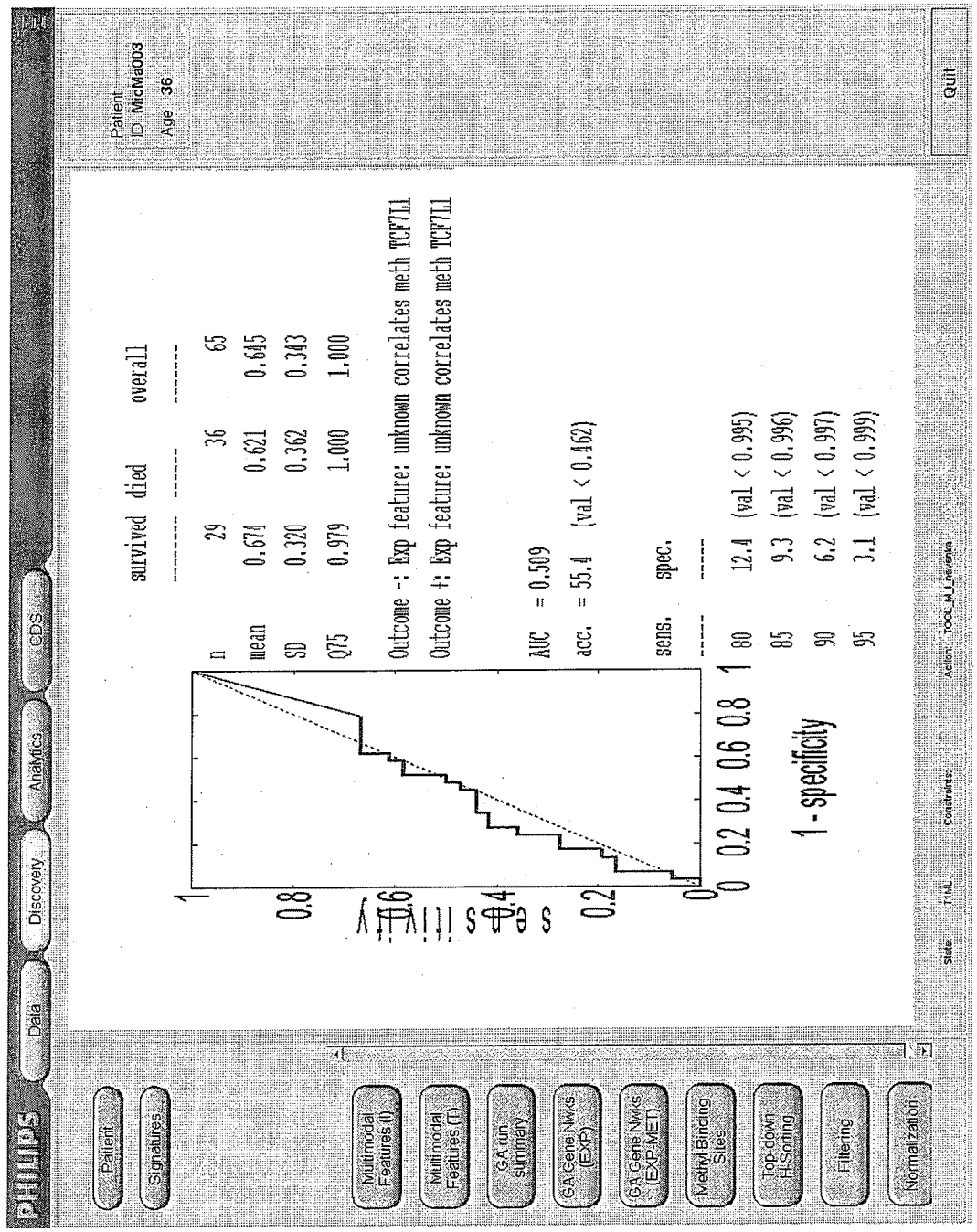
FIG. 22 shows an example of a screen related to a multimodal correlation feature analysis—graphics output.
Figure 23:
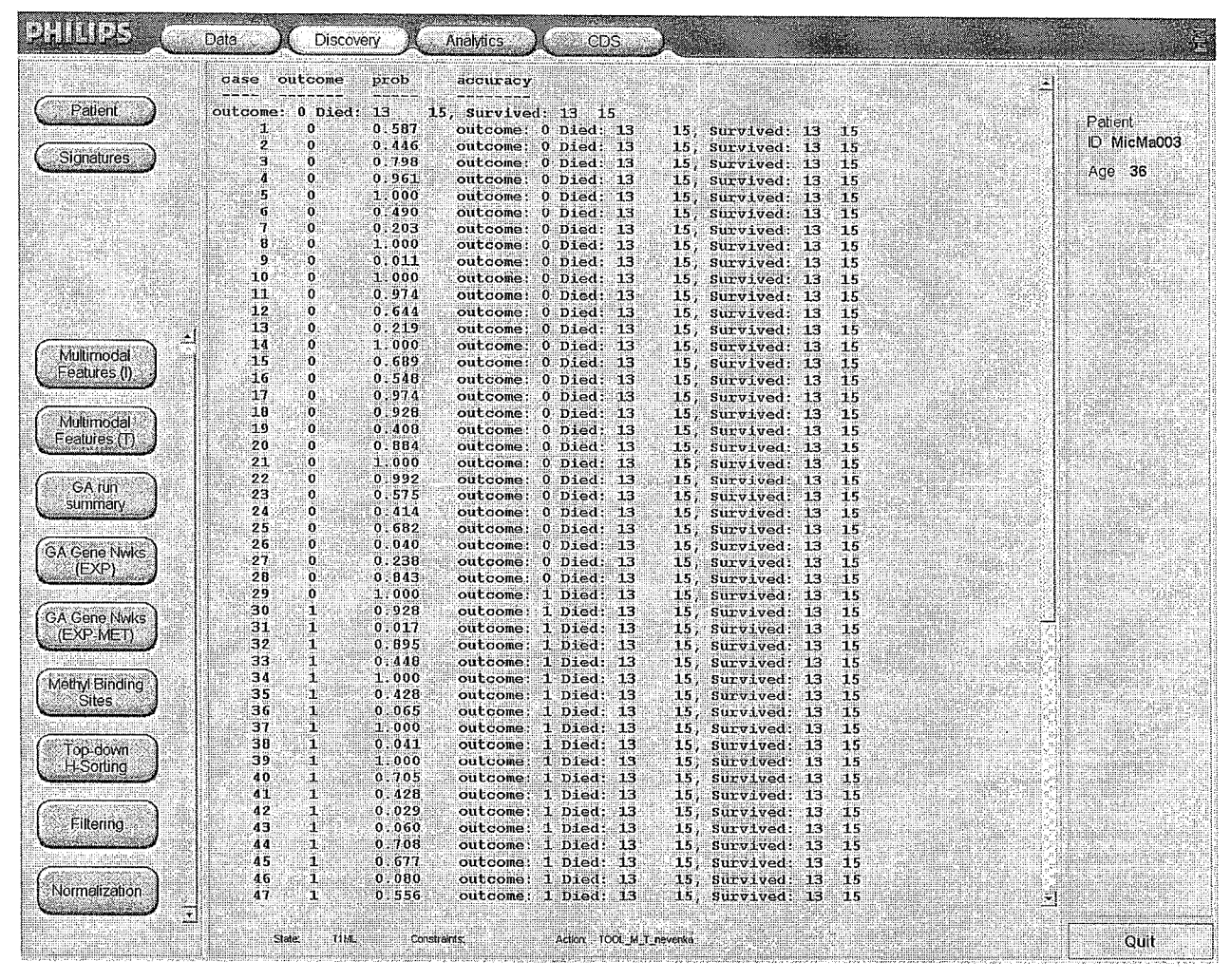
Figure 24:
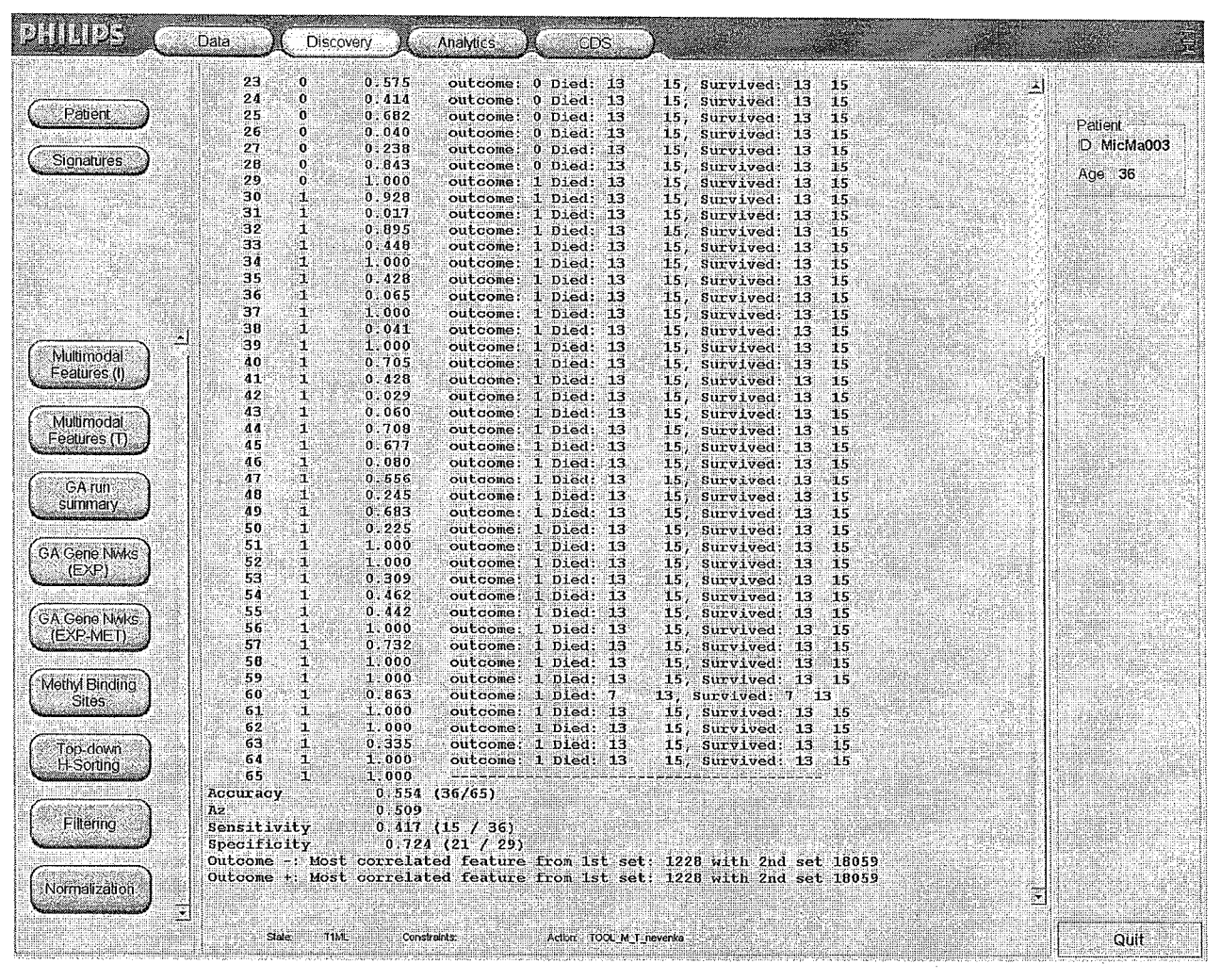

This tool shows the output of correlation between gene expression data and differential DNA methylation data. The correlation is measured based on patient outcome. The samples need to be positively correlated in the survived (positive outcome) and negatively correlated in the deceased (negative outcome) category (cf. FIG. 22). A Multimodal Feature Analysis is shown in FIGS. 23 and 24.

Example 17

Clinical Decision Support Section

The CDS Screen for Gene Expression

Figure 25:
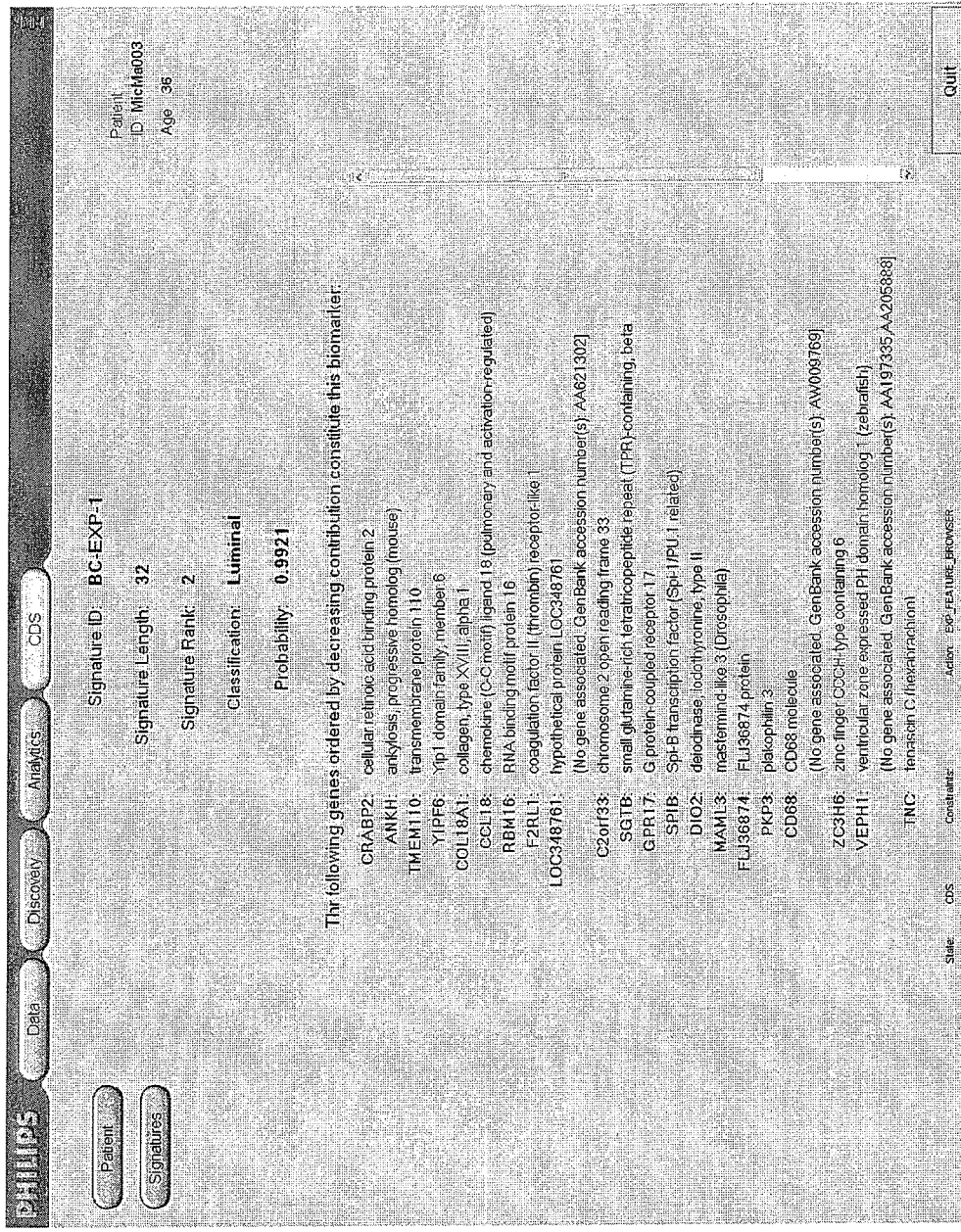
FIG. 25 shows an example of a CDS screen for gene expression.

From the signatures screen (cf. FIG. 25), the user can select a particular signature and then move to the Clinical Decision Support (CDS) screen that gives the particular patient's stratification information using the signature that was selected.

This also provides information about the rank of the signature for the given patient, the probability of the stratification prediction using the chosen signature and also the length f the signature (number of features in the signature).

This screen allows the clinical expert (user) to go back to the signatures screen or the patient data screen.

Feature Subset Selection Using a Genetic Algorithm Wrapper for a Support Vector Machines Classifier The key stage of the gene expression data analysis is the search for feature (gene) subsets which can on their own describe the entire dataset with respect to a particular labeling of the patient samples. The inventors are using a Genetic Algorithm (GA)—based tool that is designed to automatically evolve a subset of features that best predicts the ground truth labeling of the samples. In particular, the (filtered) set of gene expression data contains 3,501 gene expression probes and 104 patient samples labeled based on two breast cancer subtype groups: Luminal and Basal. The tool was run 100 times on different combinations of 78 samples for learning and 26 samples for validation. The exact same setup was repeated on data where the patient sample labels are also permuted in each of the 100 runs. This data is later used to select the statistically-significant subsets.

Among other post-processing tasks, the inventors also estimate the overall distribution of errors in millions subsets evaluated by our tool. This gives us a coarse characterization of the performance of the tool and also a convenient method to compare distinct runs. In particular, two setups of the search tool were compared. In the first one, we let the GA wrapper evolve feature subsets based solely on its classification on the 3,501×104 gene expression data. In the second setup, the inventors used classification information on around 60% of the samples from a separate analysis based on DNA methylation data. In this setup, the inventors combined the gene expression and DNA methylation (mis) classification performance to provide additional guidance in the search. The key idea is with the multi-modal approach is that the methylation data serves as an additional (orthogonal) source of information—a constraint, that will assist in the search through a vast search space.

Figure 26:
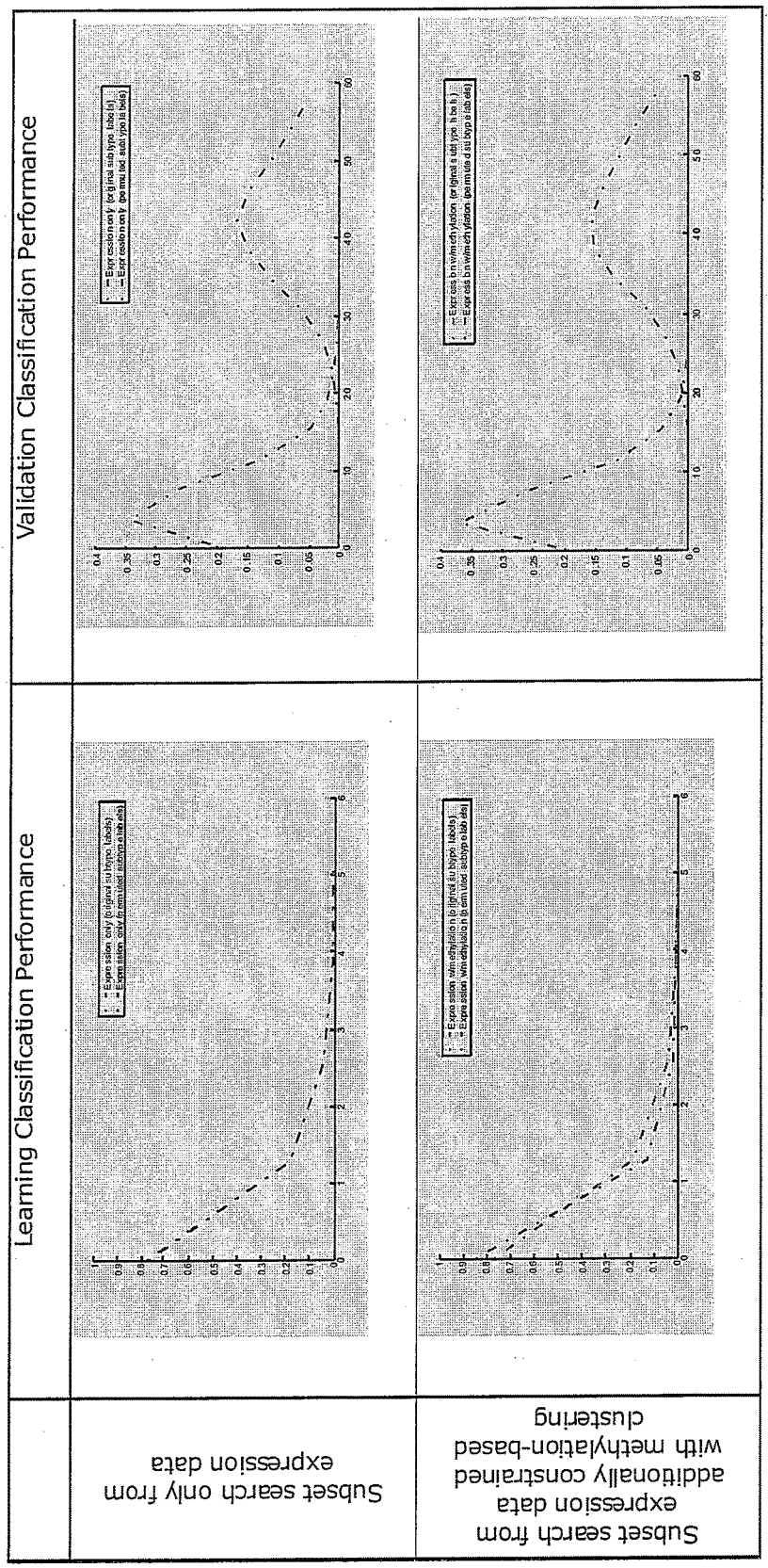
FIG. 26 shows four possible outputs of a Genetic Algorithm (GA)—based tool that is designed to automatically evolve a subset of features that best predicts the ground truth labeling of samples.

FIG. 26 shows the four possible outputs in this tool. Each graph shows the distribution of classification errors in both setups. The key observations are:

Both for the proper or the permuted labeling of the patients, the learning performance is similar both with and without the added methylation-based constraint. This is a direct result of the case-poor-feature-rich data (3,501 features vs. 78 samples), which allows the tool to fit the data to pretty much any labeling.

The validation performance plots demonstrate that our tool actually finds meaningful feature subsets. In the expression-only analysis, the validation performance (on the 26 unseen samples) is quite different from the performance on the permuted labels (median of 3.5% errors vs. 41.3% errors).

The validation performance in the methylation-constrained run also shows the same distinct validation error distribution between the proper and the permuted labels (3.2% vs. 40.8% median misclassifications), but also a slight validation performance improvement in the methylation-driven case.

Example 18

Characterizing Signatures using Statistical Significance of Learning Performance and Probability Estimates of Predicted Labels.

The GA-SVM has the ability to generate thousands of signatures with varying degrees of performance on the learning data. While the GA itself has a mechanism to choose signatures that have lower learning errors and shorter lengths, the resulting output of the GA-SVM still requires further characterization. In order to do this, the GA-SVM is independently run using 100 independent permutations of the outcome labels for the learning data. Using the output of the GA for the permuted trials, the tool estimates the parameters of the Gumbel (type-I extreme value) distribution using the distribution of learning errors across all signatures of a given size. Thus, if there are signatures of sizes ranging from 10 through 45 in the GA run, separate EVD parameters are calculated for each one of those sizes. Using the performance of the GA in discovering good-performing signatures on random data as the background distribution, the inventors can now identify whether the signatures identified by the GA on the actual data are statistically significant. Furthermore, due to the large number of gene signatures, the tool adjusts for multiple comparisons, and selects only those signatures achieving a learning performance that was extremely unlikely to have been found by chance in the given data ($p<0.05\%$). Amongst those signatures that pass this "p-value filter", the best performing ones are most likely to be larger signatures. Therefore, the tool selects 100 of the largest signatures from the pool of subsets that survived the p-value filter.

Figure 27:
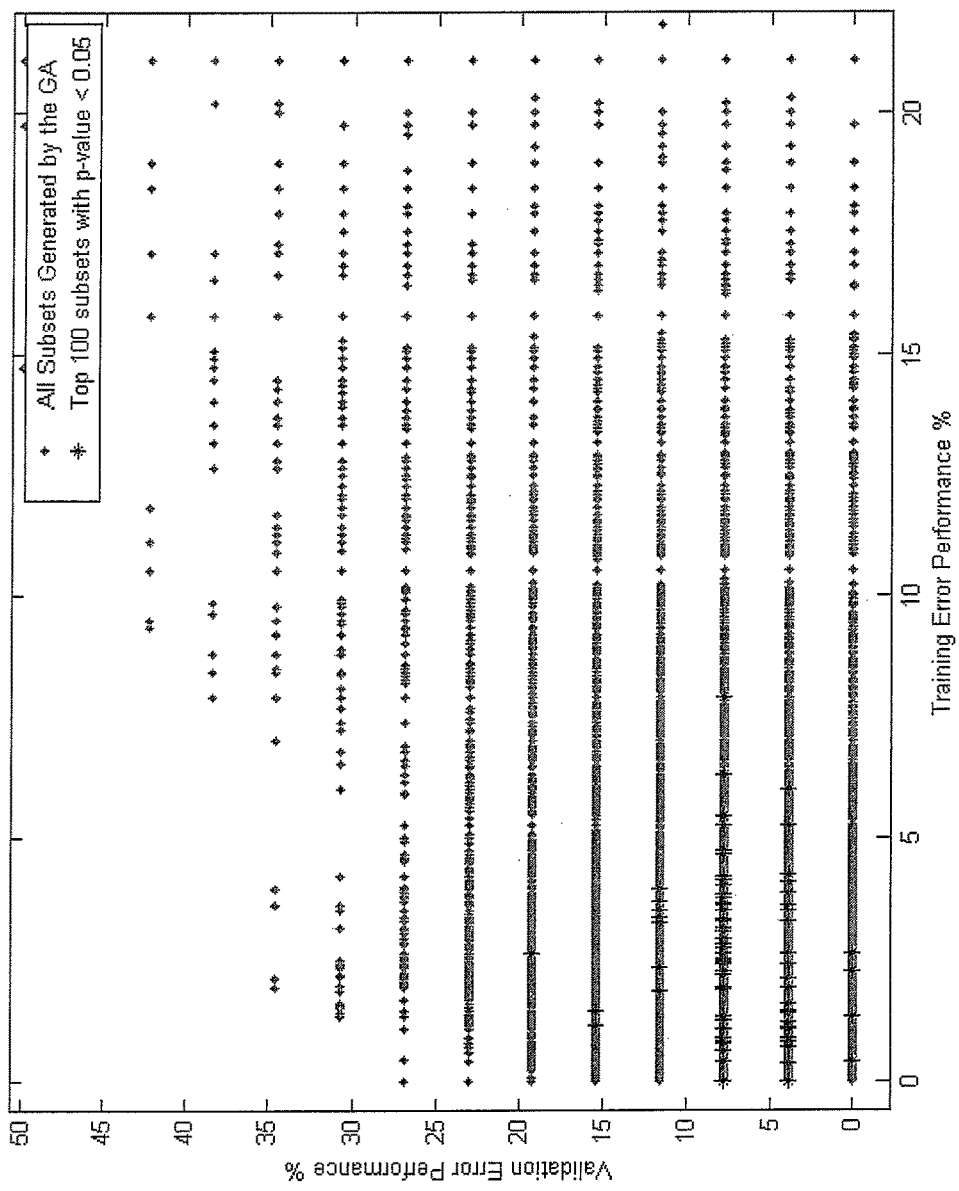
FIG. 27 shows a comparison of the performance values of all candidate feature subsets that were discovered and the feature subsets that were found significant in the post-processing analysis

As can be seen from FIG. 27, the selected signatures (in blue) have significantly better validation performance compared to all the signatures generated by the GA-SVM tool.

Finally, the selected gene expression signatures are ranked in the context of every sample based on the confidence of their predicted label for the sample. This confidence measure is a function of the distance of the sample from the hyperplane defined by the signature.

Example 19

Visualizing Gene Expression Across Patients Sorted by Clinical Annotation

Once gene signatures that discriminate patients between multiple classes are discovered, it is critical to explore and characterize the genes to get some insight into mechanisms of disease and gain confidence regarding their functional relevance. Breast cancer microarray gene expression data often provides various clinical parameters for the patient e.g. tumor grade, hormone receptor status etc. that aid the clinician in choosing an appropriate treatment plan. As an exploratory step, it is important to assess how the particular genes in the signature correlate with clinical annotations. For example, one can ask—do the genes that discriminate between luminal and basal subtypes of cancer—show clustering within a clinical annotation like hormone receptor status? If the answer is yes, the hormone receptor status (which often indicates the aggressiveness of the disease) can be linked to the particular subtypes and further hypotheses regarding mechanisms can be generated. Our Feature Browser tool enables the user to visualize the expression intensity of a gene across patients that are sorted according to a particular clinical annotation.

Figure 28:
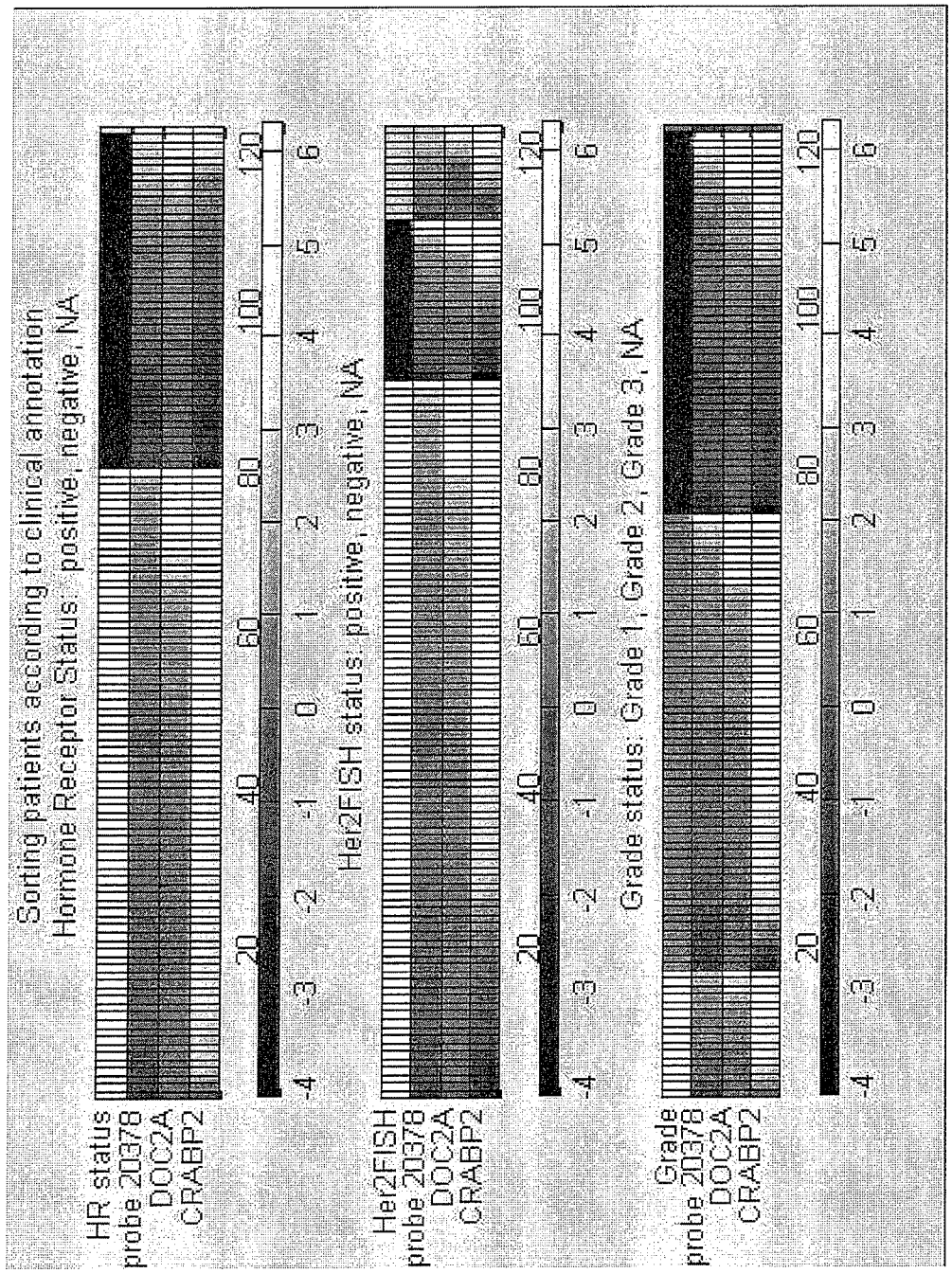
FIG. 28 shows an example of a feature browser for gene expression signatures visualizing multiple features.

The current version of the tool, focuses on three clinical annotations 1) hormone receptor status 2) Her2FISH status and 3) tumor grade (cf. FIG. 28). The inventors provide brief descriptions of each of these annotations. Hormone receptor status tests shows whether or not estrogen and/or progesterone hormones fuel the tumor. Cancer that is hormone-sensitive (e.g. ER+) is slightly slower growing and has a better chance of responding to hormone-suppression treatment, than cancer that is hormone receptor negative (e.g. ER−). Hormone-negative cancer will respond to other kinds of treatment, and hormone-suppression may not be needed. Her2FISH status determines overexpression of HER2 protein in the breast cancer tissue. This epidermal growth receptor is associated with aggressive breast cancer. HER2 positive patients are good candidates for Herceptin treatment. Tumor grade is a system used to classify cancer cells in terms of how abnormal they look under a microscope and how quickly the tumor is likely to grow and spread. Based on the microscopic appearance of cancer cells, pathologists commonly describe tumor grade by four degrees of severity: Grades 1, 2, 3, and 4. The cells of Grade 1 tumors resemble normal cells, and tend to grow and multiply slowly. Grade 1 tumors are generally considered the least aggressive in behavior. On the other hand, the cells of Grade 3 or Grade 4 tumors do not look like normal cells of the same type. Grade 3 and 4 tumors tend to grow rapidly and spread faster than tumors with a lower grade.

In the gene expression signature discovery process of the present invention, CRABP2, (cellular retinoic acid binding protein 2) is determined to be a lead discriminator. In FIG. 11, the Feature Browser tool shows that the expression of this gene is clustered according to multiple clinical annotations. Hormone receptor positive patients generally have higher levels of CRABP2 expression than hormone receptor negative patients. From the visualization, one might speculate that CRABP2 is related to the hormone receptor pathway of the disease. FIG. 28 shows CRABP2 in the context of two other genes that do not appear to follow the same pattern. A quick literature search reveals that the retinoic acid pathway is important in cancer progression.

Example 20

Tool for Visualizing the Meta-Data of a Gene Signature

The purpose of this tool is to provide visualization of the meta-data associated with a gene signature. Gene signatures are subsets of genes that could be generated by statistical methods such as genetic algorithms. Further description on the generation of the signatures is included in the section titled: Feature Subset Selection Using a Genetic Algorithm Wrapper for Support Vector Machines Classifier.

An example of a meta-data source is the Gene Ontology (GO). The Gene Ontology is a controlled vocabulary of terms organized as an acyclic directed graphs. This ontology is split into three related ontologies covering basic areas of molecular biology: the molecular function of gene products, their role in multi-step biological processes, and their localization to cellular components. Researchers worldwide annotate gene products, i.e., characterize gene products using terms from the ontology, and submit them to the GO project to be included in gene annotation files. In a gene annotation file, each annotation is an association of a single gene product with a single GO term. A gene product can be annotated by terms indicating the cellular components it is located in, its molecular functions, and the biological processes it participates in.

Figure 29:
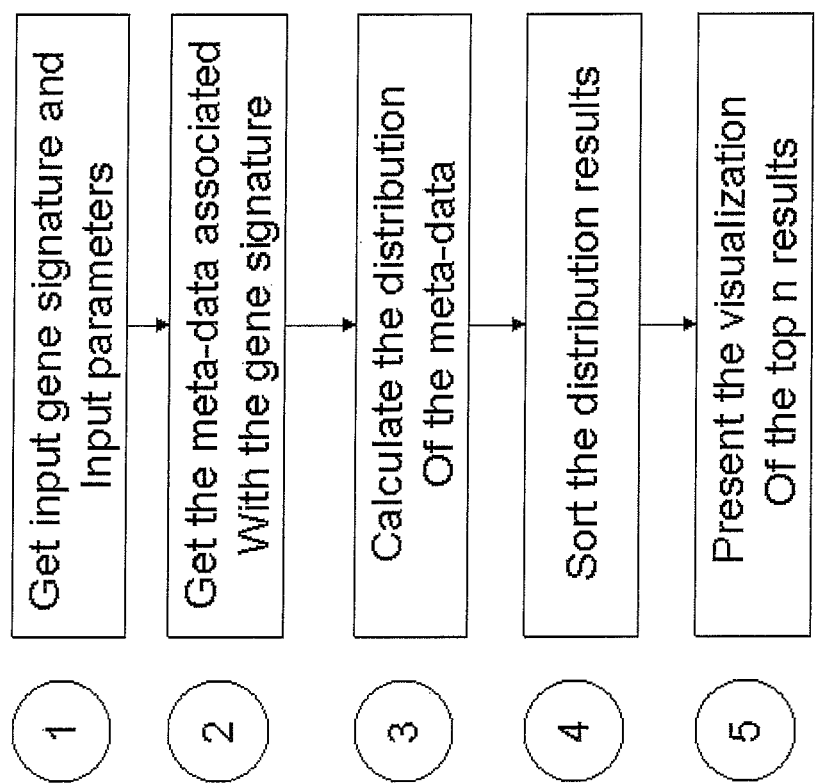
FIG. 29 shows a flowchart describing the process of generating the visualization of a gene signature meta-data.
Figure 30:
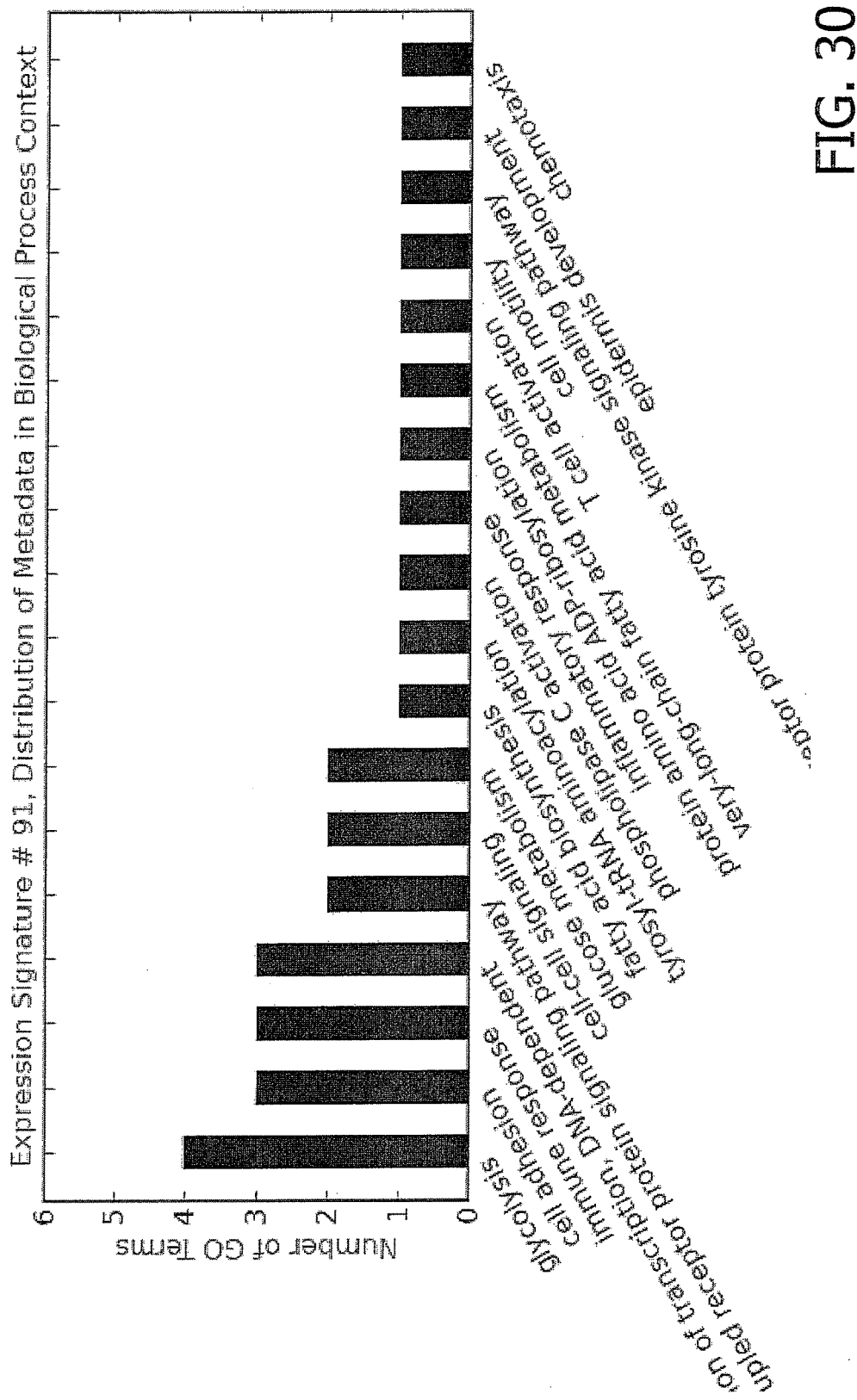
FIG. 30 shows an example of presenting the distribution of gene signature meta-data.

The annotations (meta-data) of genes in a signature provide an understanding of the biological meaning of the signature as some meta-data may be more abundant than others. The following paragraph describes the process of generating the visualization of a gene signature meta-data. A flowchart describing this process is depicted in FIG. 29.
1. Get the gene signature, the desired biological context, and the display parameters. The gene signature can be an index to list of that contain gene subsets. The user defines the biological context to be explored. Examples of biological contexts are Cellular Component, Molecular Function, and Biological Process. The user can also define the presentation parameters, such as the number of items to be presented, and the display mode of full screen or half screen.
2. Get the meta-data associated with the gene signature. For example, obtain the Gene Ontology annotations associated with the genes in the signature. Furthermore, these annotations can be limited to a biological context defined by the user.
3. Calculate the distribution of the meta-data. For example, it calculates the distribution of the Gene Ontology annotations that were previously collected.
4. Sort the distributions in descending or ascending order.
5. Present in a visual aid (e.g. histogram) the top n distributions. An example of this display is depicted in FIG. 30.

Example 21

Finding Methyl-Binding Protein DNA Binding Sites

The program identifies methyl binding sites in DNA sequences. The tool has been designed to work with microarray probes and recognize specific patterns within these probe sequences.

The inventors apply the pattern search to differentially methylated sequences. Our CpG island array contains CpG islands genome-wide. Based on the hybridization experiments followed by statistical analysis we obtain a set of loci (probes/sequences) which are differentially methylated. This enables easier biological interpretation of the results. The inputs to the program include:
1. Index file—This file contains a list of indices that correspond to the MspI fragments on which we wish to perform the analysis. The first line of the index file is considered header information and not processed.
2. Microarray Probes annotation file—This file contains the probe IDs, their sequence, and other relevant information. For the MOMA array, the information that is processed includes:

a. MspFrag IDs
b. Sequence
c. Neighboring genes and their distance to the Msp fragment. These values are listed for both 5' and 3' directions and both on sense and anti-sense strands.

The first line is considered to be the header information and is not processed.
The overall flow of the program is as follows:
1. Feed the microarray annotation file into an array.
2. For each index in the index file, extract the corresponding row from the annotation file array. There is a direct correspondence between the index number specified in the index file and the row number of the corresponding MspFragment.
3. Split the Msp Fragment row into an array of values.
4. Calculate the nearest gene to the MspFragment.
5. Perform a simple regular expression match to check for the list of methyl binding sites on the sequence of the Msp fragment (accessed by its position in the row array).
6. Print the hits to a file along with the nearest gene and the minimum distance.

The program prints out a file with:
1. The particular pattern or the methyl binding site identified
2. The MspFragID
3. The nearest gene to the Msp fragment (gene symbol)
4. The distance to the nearest gene.

Sample Printout:

| Kaiso: | MspFrag129193 | 355698 | KIAA0427 |
| Kaiso: | MspFrag87210 | 482172 | BC033889 |
| Kaiso: | MspFrag139352 | 99006 | AK074590 |
| MeCP2: | MspFrag145432 | 293059 | CEBPB |
| Kaiso: | MspFrag6016 | 12977 | MGC15668 |
| MeCP2: | MspFrag148218 | 1146 | ZNF295 |
| MeCP2: | MspFrag121388 | 357633 | LHX1 |
| Kaiso: | MspFrag27766 | 1055474 | GPR27 |
| MeCP2: | MspFrag27766 | 1055474 | GPR27 |
| Kaiso: | MspFrag86939 | 326583 | LRP5 |
| MeCP2: | MspFrag86939 | 326583 | LRP5 |
| Kaiso: | MspFrag150179 | 219969 | BCR |
| Kaiso: | MspFrag46871 | 24399 | HLA-F |
| MZIF: | MspFrag46871 | 24399 | HLA-F |
| Kaiso: | MspFrag108348 | 22589 | AK000173 |
| MeCP2: | MspFrag137260 | 269802 | ZNF507 |
| Kaiso: | MspFrag47714 | 14469 | BC091488 |
| MeCP2: | MspFrag1006 | 61125 | BC065369 |
| Kaiso: | MspFrag110545 | 131366 | AK127296 |
| MeCP2: | MspFrag128335 | 813522 | GATA6 |
| MeCP2: | MspFrag152493 | 3200 | CELSR1 |
| Kaiso: | MspFrag42758 | 341720 | CXXC5 |
| Kaiso: | MspFrag144741 | 4395 | MAFB |

Example 22

Top Down Hierarchical Sorting

The method sorts the rows based on the values found in each column and detects and groups those rows exhibiting one or more strong patterns in the same column. With this sorting method content in distinct columns is analyzed individually.

Since patterns are searched on individual columns and no global metric needs to be computed across the columns, our method is well suited for parallelization, as opposed to standard clustering algorithms.

In the tool this method is applied as a sorting (clustering) approach to detect patterns in microarray experimental data. The problem with microarray data is that there is huge disparity of number of probes (features) vs. number of samples. By focusing on single gene (or locus) the influence of single genes on the entire classification and subset selection problem is shown. By focusing on single data sample/patient the inventors can detect genes similarly expressed for each sample/patient.

In the example provided the columns represent data samples while rows represent methylation levels of the genes (loci) in the microarray for that specific data sample. Each data sample can originate from different patients, or from different tissue of one patient.

The Sorting Method Proceeds as Follows:

Derives histograms of the values in each column

Sorts rows based on histogram comparison for each column

Build Histograms

For each column, values that are "similar" are grouped together and histograms showing the number of values falling in each bin are built.

Sorting

Next, for each column one or more histogram bins are selected, according to specific criteria (e.g. the largest bin). Based on the histogram bins, the domain is then split according to a chosen algorithm into groups of rows (clusters) and the selection process is repeated in each of the subdomains until a stopping criterion is reached. Based on the clusters that are generated, the same algorithm specifies the required permutations on the rows (sorting).

Figure 31:
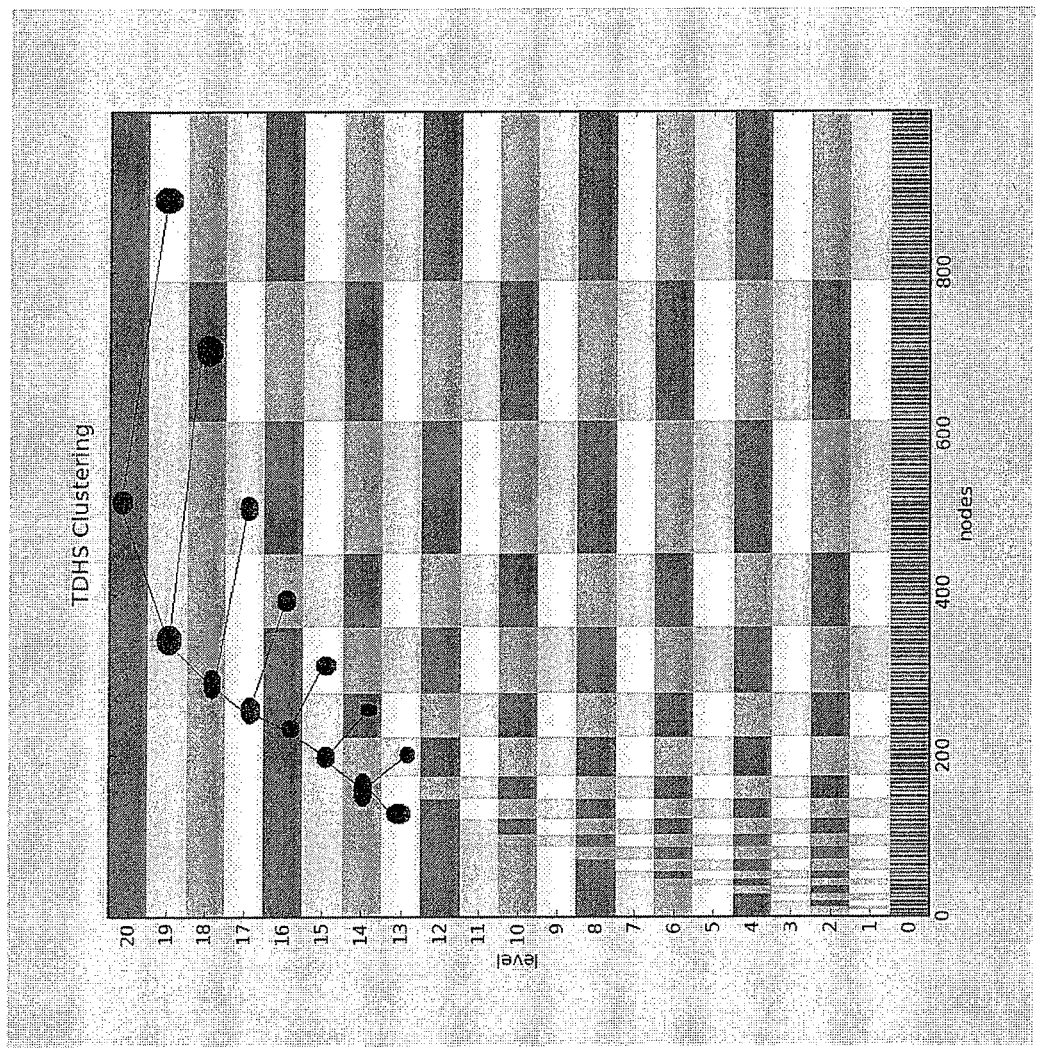
FIG. 31 show an example of Top Down Hierarchical Sorting (TDHS).

Perform Top Down Hierarchical Sorting (TDHS)—FIG. 31.

With TDHS first the longest pattern (i.e. the one that corresponds to the largest histogram bin) in any of the columns is computed. The largest histogram bin provides the largest number of rows that share a "similar" value. Once the largest value in all histograms across all columns (for each column there is a single histogram) is found, the column of the largest histogram is selected and the rows contributing to the longest histogram bin (i.e. longest pattern) are grouped together. Based on the longest pattern, TDHS splits the domain of rows into those containing the longest pattern and the rest. The whole domain of rows is split this way into the group sharing a similarity in that column and the rest, obtaining two "clusters" (although this is not a clustering algorithm in the strict sense of the word we adopt this terminology). In the next iterations, histograms of the values are built again or the computed histograms are updated to reflect the split into clusters. In each of the two clusters, the (next) longest histogram bin is selected and the domain is again split into two clusters. The iterations stop when the size of the longest histogram is below a predefined threshold, when the user-defined number of long patterns to be extracted was reached, or when each of the two clusters contains a single row. In the end we will have a hierarchy of patterns. We can choose to display at each step either both clusters or only the one with the longest pattern. This strategy may miss patterns (or parts of) when they are split in a previous step. One variation on TDHS is to stop splitting one side of the tree—the one that already contains the longest pattern. This will result in a one-sided multi-leaved binary tree.

Example 23

Figure 32:
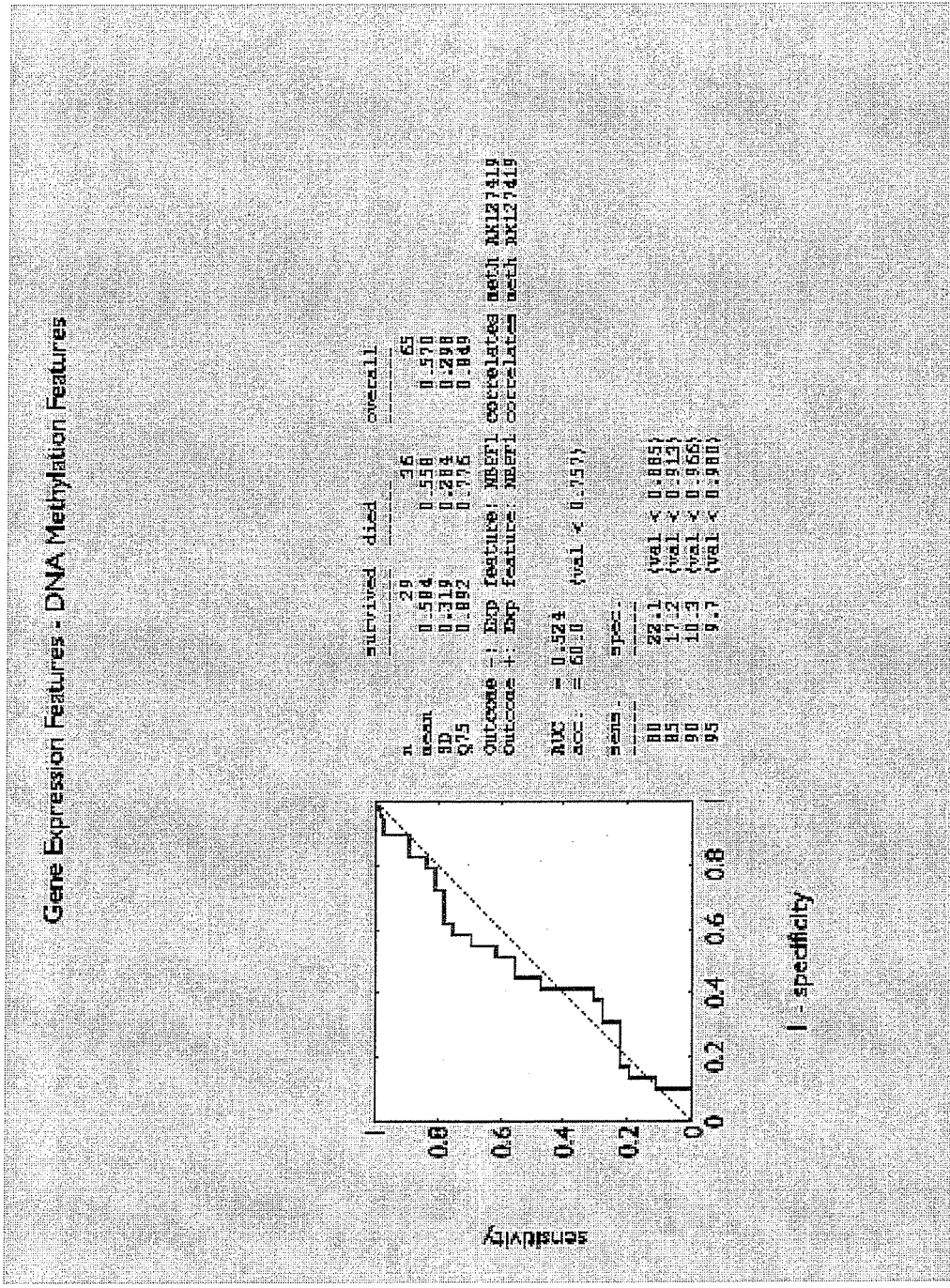
FIG. 32 shows an example of the correlation of gene expression and DNA methylation data.

Correlation of Gene Expression and DNA Methylation Data (FIG. 32)

The tool uses statistical correlation between gene expression features and differential DNA methylation order to find genes (features) that are strongly correlated with loci in other modality. We use a method to correlate features from one modality (RNA and DNA Methylation) to other and find the features that are most highly correlated and predictive in order to predict the outcome of an unknown case. We select the pair of features that correlate the best in case of one indication (benign/survived) and selection of another pair of features in case of opposite indication (malignant/died). A regression model is generated of the pairs of features for prediction. Based on this regression model, we predict an unknown case's indication. While training we use a leave-one-out method: all the patient cases but one are used for training and one case is used for testing.

The method is used in two possible modes based on the supplied data:
1. Only best performing signatures from gene expression data set vs. Best performing signatures from differential DNA methylation dataset.
2. All gene expression features are correlated vs. all differential DNA methylation loci.

Example 24

Visualizing Fragment Methylation Across Patients Sorted by Subtype

It is critical to explore and characterize the fragments that are involved in the disease pathology on a fragment by fragment basis to get some insight into their functional relevance. Breast cancers have various clinical parameters for the patient e.g. tumor grade, hormone receptor status etc. and the cancers can be subgrouped in different types. As an exploratory step, it is important to assess how the particular fragment in the signature correlates with these subgroups.

The current version of the tool, plots the given fragments methylation status in the given patient in conjunction with a set of patients chosen from the database. The patients are grouped according to their subgroup and the patient methylation status is highlighted in a black rectangle.

Example 25

Visualizing Cluster Dendrogram of the Patients According to Hierarchical Clustering When a signature is obtained, it is important to look how the signature groups patients into various subtypes. This type of visualization is possible both for gene expression data as well as for DNA methylation data. Then we can see if the different subgroups are relevant in a clinical setting—such as with regard to outcome, histopathology, receptor status etc.

For a given signature, we perform hierarchical clustering using Pearson correlation as a distance metric. The dendrogram output is then annotated using clinical parameters such as ER status. The given patient in the cluster is denoted by an X. Then the clinician can make a determination if the patient is classified as being in a group with a high or low risk of recurrence, ER status etc. Also the dendrogram gives an idea of how the patient may belong to an atypical group. Sometimes, the clinical parameters may indicate that the patient may be responsive to therapy and belonging to a ER positive subgroup. But in the context of the signature, the patient may be classified as belonging to the ER negative group with bad prognosis. Here the clinician may have to treat this patient as possibly having a bad risk profile according to the subgrouping even though the classical clinical parameters indicate otherwise.

In final two examples, a conceptual series of steps is described that include most key innovative aspects of the presented invention. The system is given high-throughput (gene expression and DNA methylation) and clinical data for 200 patients with a survival follow-up of at least 10 years for all patients. The data is loaded in the internal database and the system is configured to use the tools described in the text of this invention.

Example 26

In this example, the gene expression data is analyzed using a series of tools that are available to the user as the analysis progresses. Initially, the user select one of the filtering tools and based on this selection, the context of the analysis is set for gene expression and the next set of available tools is for example genetic algorithm wrapper around a classifier designed for gene expression data. The result of this analysis is a set of candidate signatures that the researcher can analyze and prioritize based on the application of additional available tools in this context. One of these tools is to re-analyze the data using the DNA methylation measurements as an additional input to the genetic algorithm for feature subset selection. The output of this is an additional set of candidate signatures that the researches can again analyze and prioritize using more tools registered with the system. In the end one or more if these signatures are selected of clinical validation and the research portion of the PAPAyA application is complete. The key to this aspect of the innovation is to continuously provide the user with the applicable tools in the context of the analysis which include the selected modality and the stage in the pipeline (e.g. pre-processing, analysis, or post-processing).

Example 27

In this example, one or more candidate signatures discovered in the research mode of the invention have been validated and molecular diagnostic tests are available to the clinical and are part of the clinical practice. The clinical decision support mode of the application allows the clinical to view the molecular profiles of the patient, but more importantly, the system will provide based on the context access to tools that allow for visualization and processing of the patient data in the context of other clinical studies. For example, the clinical may want to view the patient's profile in the context of the original clinical study that determined the signature on which the diagnostic test is based. Again, the system maintains the current context of the decision support interaction and provides the clinical with the relevant tools that allow for switch between molecular and clinical modalities and other relevant sources of data.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A medical analysis system for pre-clinical and/or clinical analysis of data obtained from at least one patient, the system comprising:
    an internal database (IDB), the database comprising a collection of data, analysis results, flow definitions, and tool definitions, and other related data for tools that utilize a database repository,
    a database access unit (DA), the unit that provides access to the internal database,
    a flow definition unit (FD), the unit providing execution of a configurable flow of analysis and visualization of a plurality of data modalities, the plurality of data modalities comprising:
    a first bio-molecular modality comprising bio-molecular data related to the patient, and
    a second clinical modality comprising clinical data related to the patient,
    a tool execution engine (TEE), having an interface for the system to configure and instantiate one or more tools working on one or more of the data modalities,
    a tool repository, the repository comprising a collection of tools for which the system is configured to execute, said tools complying with a set of rules in order for it to be possible to visualize their execution in a graphical user interface (GUI),
    one or more associated external databases (EDB), the external database(s) representing data stored in the said system itself, or in a database different from the said internal database (IDB), and
    a graphical user interface (GUI), said interface simultaneously visualizing data, analysis results, and outcome of one or more tool executions, and wherein said interface further simultaneously visualizes:
    1) an outcome of said first bio-molecular modality, and
    2) an outcome of said second clinical modality.

2. The medical analysis system according to claim 1, wherein the medical analysis system is applied to at least one patient in an in pre-clinical situation.

3. The medical analysis system according to claim 1, wherein said analysis system is applied to a group of patients.

4. The medical analysis system according to claim 1, wherein said analysis system is applied to one patient in a clinical situation.

5. The medical analysis system according to claim 1, wherein the medical analysis system is a functioning as a clinical decision support system (CDS).

6. The medical analysis system according to claim 1, wherein said first bio-molecular modality and said second clinical modality is integrateable by a machine learning algorithm, the result of said integration being visualizable in the graphical user interface.

7. The medical analysis system according to claim 1, wherein said first bio-molecular modality and said second clinical modality is integrateable by a statistical algorithm, the result of said integration being visualizable in the graphical user interface.

8. The medical analysis system according to claim 1, wherein said first bio-molecular modality and said second clinical modality is integrateable based on their respective genomic annotation, the result of said integration being visualizable in the graphical user interface.

9. The medical analysis system according to claim 1, wherein
said first bio-molecular modality is based on a high-throughput data sampling modality.

10. The medical analysis system according to claim 9, wherein the sample provided by said high-throughput data sampling modality comprise data on at least 100.000 parameter/species.

11. The medical analysis system according to claim 1, wherein said first bio-molecular modality is selected from the group consisting of a high-throughput gene expression profiling, DNA methylation status profiling, comparative genomic hybridization analysis.

12. The medical analysis system according to claim 1, wherein said flow definition unit (FD) comprises at least one further bio-molecular modality.

13. The medical analysis system according to claim 1, wherein said further bio-molecular modality is selected from the group consisting of a high-throughput gene expression profiling, DNA methylation status profiling, comparative genomic hybridization analysis, and SNP profile.

14. The medical analysis system according to claim 13, wherein
said patient has a clinical condition selected from the group consisting cancer, a cardiovascular disease, a metabolic disease, a gastro-intestinal disease, a neurological disease.

15. The medical analysis system of claim 1, wherein said system further discovers a bio-molecular or clinical signature associated with a specific clinical condition.

16. The medical analysis system according to claim 15, wherein the clinical condition is selected from the group consisting of cancer, a cardiovascular disease, a metabolic disease, a gastro-intestinal disease, a neurological disease.

17. The medical analysis system according to claim 16, wherein said cancer is breast cancer or colon cancer.

18. The medical analysis system according to claim 1, wherein said signature is a gene expression signature, DNA methylation status signature, comparative genomic hybridization signature and SNP signature.

19. A medical analysis process for pre-clinical and/or clinical analysis of data obtained from at least one patient, the process comprising:
executing, with a flow definition unit (FD), a configurable flow of analysis and visualization of a plurality of data modalities, the plurality of data modalities comprising:
a first bio-molecular modality comprising bio-molecular data related to the patient, and
a second clinical modality comprising clinical data related to the patient, instantiating, with a tool execution engine (TEE), one or more tools working on one or more of the data modalities, wherein the TEE has an interface for the system to configure wherein a tool repository comprises a collection of tools for which the system is configured to execute, and the tools comply with a set of rules to visualize their execution in a graphical user interface (GUI),
simultaneously visualizing, with the GUI, data, analysis results, and an outcome of one or more tool executions, and further simultaneously visualizing an outcome of said first bio-molecular modality, and an outcome of said second clinical modality,
wherein an internal database (IDB) comprises a collection of data, the analysis results, flow definitions, and tool definitions, and other related data for tools that utilize a database repository, wherein a database access unit (DA) provides access to the internal database, and wherein one or more associated external databases (EDB) represents data stored in the system itself, or in a database different from the internal database (IDB).

20. A memory of a computer arrangement loaded with a computer program product comprising instructions for performing a pre-clinical and/or clinical analysis of data obtained from at least one patient, the computer arrangement comprising a processing unit and the memory, wherein the computer program product when executed by the processing unit causes the processing unit to:
execute, with a flow definition unit (FD), a configurable flow of analysis and visualization of a plurality of data modalities, the plurality of data modalities comprising:
a first bio-molecular modality comprising bio-molecular data related to the patient, and
a second clinical modality comprising clinical data related to the patient,
instantiate, with a tool execution engine (TEE), one or more tools working on one or more of the data modalities, wherein the TEE has an interface fir the system to configure, wherein a tool repository comprises a collection of tools for which the system is configured to execute, and the tools comply with a set of rules to visualize their execution in a graphical user interface (GUI),
simultaneously visualize, with the GUI, data, analysis results, and an outcome of one or more tool executions, and further simultaneously visualize an outcome of said first bio-molecular modality, and an outcome of said second clinical modality,
wherein an internal database (IDB) comprises a collection of data, the analysis results, flow definitions, and tool definitions, and other related data for tools that utilize a database repository, wherein a database access unit (DA) provides access to the internal database, and wherein one or more associated external databases (EDB) represents data stored in the system itself, or in a database different from the internal database (IDB).

* * * * *